US008829166B2

(12) United States Patent
Thorne et al.

(10) Patent No.: US 8,829,166 B2
(45) Date of Patent: *Sep. 9, 2014

(54) RAPID ISOLATION OF OSTEOINDUCTIVE PROTEIN MIXTURES FROM MAMMALIAN BONE TISSUE

(75) Inventors: Kevin Thorne, Austin, TX (US); Rama Akella, Austin, TX (US)

(73) Assignee: Zimmer Orthobiologics, Inc., Austin, TX (US)

( * ) Notice: Subject to any disclaimer, the term of this patent is extended or adjusted under 35 U.S.C. 154(b) by 777 days.

This patent is subject to a terminal disclaimer.

(21) Appl. No.: 12/582,476

(22) Filed: Oct. 20, 2009

(65) Prior Publication Data

US 2010/0041611 A1 Feb. 18, 2010

Related U.S. Application Data

(63) Continuation of application No. 11/553,640, filed on Oct. 27, 2006, now Pat. No. 7,622,562, which is a continuation-in-part of application No. 10/606,190, filed on Jun. 25, 2003, now Pat. No. 7,241,874.

(60) Provisional application No. 60/391,566, filed on Jun. 26, 2002.

(51) Int. Cl.
| C07K 14/51 | (2006.01) |
| C07K 14/145 | (2006.01) |
| C07K 1/14 | (2006.01) |
| C07K 1/34 | (2006.01) |
| A61K 38/17 | (2006.01) |

(52) U.S. Cl.
USPC ......... 530/412; 530/840; 514/21.92; 424/549

(58) Field of Classification Search
USPC ............. 530/840, 412; 514/21.92; 424/549
See application file for complete search history.

(56) References Cited

U.S. PATENT DOCUMENTS

| 3,318,774 A | 5/1967 | Dingwall et al. | |
| 3,458,397 A * | 7/1969 | Millonig et al. | 435/325 |
| 3,471,598 A | 10/1969 | Battista | |
| 3,867,728 A | 2/1975 | Stubstad et al. | |
| 3,927,205 A | 12/1975 | Ohno et al. | |
| 3,949,073 A | 4/1976 | Daniels et al. | |
| 4,002,602 A | 1/1977 | Goldstein | |
| 4,066,083 A | 1/1978 | Ries | |
| 4,172,128 A | 10/1979 | Thiele et al. | 424/95 |
| 4,294,753 A * | 10/1981 | Urist | 530/395 |
| 4,327,982 A | 5/1982 | Yamamichi et al. | |
| 4,389,487 A | 6/1983 | Ries | |
| 4,394,370 A | 7/1983 | Jefferies | |
| 4,412,947 A | 11/1983 | Cioca | |
| 4,413,359 A | 11/1983 | Akiyama et al. | |
| 4,434,094 A | 2/1984 | Seyedin et al. | |
| 4,440,750 A | 4/1984 | Glowacki et al. | |
| 4,455,256 A | 6/1984 | Urist | 260/112 R |
| 4,516,276 A | 5/1985 | Mittelmeier | |
| 4,529,590 A | 7/1985 | LeVeen et al. | |
| 4,559,299 A | 12/1985 | Rotman | |
| 4,563,350 A | 1/1986 | Nathan et al. | |
| 4,596,574 A | 6/1986 | Urist | 623/16 |
| 4,608,199 A | 8/1986 | Caplan et al. | |
| 4,609,551 A | 9/1986 | Caplan et al. | |
| 4,619,989 A | 10/1986 | Urist | 530/417 |
| 4,620,327 A | 11/1986 | Caplan et al. | |
| 4,627,853 A | 12/1986 | Campbell et al. | |
| 4,627,982 A | 12/1986 | Seyedin et al. | |
| 4,637,931 A | 1/1987 | Schmitz | |
| 4,663,358 A | 5/1987 | Hyon et al. | |
| 4,678,470 A | 7/1987 | Nashef et al. | |
| 4,681,763 A | 7/1987 | Nathanson et al. | |
| 4,699,788 A | 10/1987 | Catsimpoolas et al. | |
| 4,743,259 A | 5/1988 | Bolander et al. | 623/16 |
| 4,761,471 A | 8/1988 | Urist | |
| 4,772,287 A | 9/1988 | Ray et al. | |
| 4,774,227 A | 9/1988 | Piez et al. | |
| 4,774,228 A | 9/1988 | Seyedin et al. | |
| 4,774,322 A | 9/1988 | Seyedin et al. | |
| 4,789,663 A | 12/1988 | Wallace et al. | |
| 4,789,732 A | 12/1988 | Urist | |
| 4,795,467 A | 1/1989 | Piez et al. | |
| 4,795,804 A | 1/1989 | Urist | |
| 4,801,299 A | 1/1989 | Brendel et al. | |

(Continued)

FOREIGN PATENT DOCUMENTS

| AU | 199871003 B2 | 10/1998 |
| CA | 2285382 | 10/1998 |

(Continued)

OTHER PUBLICATIONS

Folkman, "Angiogenic Therapy of the Human Heart," American Heart Association 97:628-629 (1998).

(Continued)

*Primary Examiner* — Vera Afremova
(74) *Attorney, Agent, or Firm* — Schwegman Lundberg & Woessner, P.A.

(57) ABSTRACT

A method for purifying bone-derived osteoinductive proteins including a demineralization process, a protein extraction process, a high molecular weight ultrafiltration process, a low molecular weight ultrafiltration process, and a recover process. The high and low ultrafiltration processes preferably select proteins having a nominal molecular weight between approximately 8 kilodaltons and approximately 100 kilodaltons. Processes of the present invention may be used to recover osteoinductive proteins from bone demineralization waste streams.

29 Claims, No Drawings

(56) References Cited

U.S. PATENT DOCUMENTS

| | | | | |
|---|---|---|---|---|
| 4,804,744 | A | 2/1989 | Sen | |
| 4,810,691 | A | 3/1989 | Seyedin et al. | |
| 4,834,757 | A | 5/1989 | Brantigan | |
| 4,843,063 | A | 6/1989 | Seyedin et al. | |
| 4,863,732 | A | 9/1989 | Nathan et al. | |
| 4,874,746 | A | 10/1989 | Antoniades et al. | 514/21 |
| 4,877,864 | A | 10/1989 | Wang et al. | |
| 4,888,366 | A | 12/1989 | Chu et al. | |
| 4,894,744 | A | 1/1990 | Talbot et al. | |
| 4,902,296 | A | 2/1990 | Bolander et al. | 623/16 |
| 4,904,260 | A | 2/1990 | Ray et al. | |
| 4,950,483 | A | 8/1990 | Ksander et al. | |
| 4,952,404 | A | 8/1990 | Vallee et al. | |
| 4,968,590 | A | 11/1990 | Kuberasampath et al. | |
| 4,975,526 | A | 12/1990 | Kuberasampath et al. | |
| 4,975,527 | A | 12/1990 | Koezuka et al. | |
| 4,992,226 | A | 2/1991 | Piez et al. | |
| 5,001,169 | A | 3/1991 | Nathan et al. | |
| 5,002,583 | A | 3/1991 | Pitaru et al. | |
| 5,015,255 | A | 5/1991 | Kuslich | |
| 5,047,055 | A | 9/1991 | Bao et al. | |
| 5,053,050 | A | 10/1991 | Itay | |
| 5,100,422 | A | 3/1992 | Berguer et al. | |
| 5,108,438 | A | 4/1992 | Stone | |
| 5,116,738 | A | 5/1992 | Wang et al. | |
| 5,118,667 | A | 6/1992 | Adams et al. | |
| 5,141,905 | A | 8/1992 | Rosen et al. | |
| 5,147,374 | A | 9/1992 | Fernandez | |
| 5,152,791 | A | 10/1992 | Hakamatsuka et al. | |
| 5,171,278 | A | 12/1992 | Pisharodi | |
| 5,187,076 | A | 2/1993 | Wozney et al. | |
| 5,192,326 | A | 3/1993 | Bao et al. | |
| 5,206,023 | A | 4/1993 | Hunziker | |
| 5,208,219 | A | 5/1993 | Ogawa et al. | |
| 5,219,576 | A | 6/1993 | Chu et al. | |
| 5,236,456 | A | 8/1993 | O'Leary et al. | 623/16 |
| 5,256,644 | A | 10/1993 | Antoniades et al. | 514/12 |
| 5,258,043 | A | 11/1993 | Stone | |
| 5,260,763 | A | 11/1993 | Yamashita | |
| 5,270,300 | A | 12/1993 | Hunziker | |
| 5,290,558 | A | 3/1994 | O'Leary et al. | 424/422 |
| 5,290,763 | A | 3/1994 | Poser et al. | 514/21 |
| 5,306,311 | A | 4/1994 | Stone et al. | |
| 5,314,477 | A | 5/1994 | Marnay | |
| 5,322,933 | A | 6/1994 | Davies et al. | |
| 5,332,802 | A | 7/1994 | Kelman et al. | |
| 5,356,630 | A | 10/1994 | Laurencin et al. | |
| 5,368,858 | A | 11/1994 | Hunziker | |
| 5,371,191 | A | * 12/1994 | Poser et al. | 530/350 |
| 5,387,213 | A | 2/1995 | Breard et al. | |
| 5,390,683 | A | 2/1995 | Pisharodi | |
| 5,393,739 | A | 2/1995 | Bentz et al. | 514/12 |
| 5,403,825 | A | * 4/1995 | Lagarde et al. | 514/7.6 |
| 5,425,772 | A | 6/1995 | Brantigan | |
| 5,464,439 | A | 11/1995 | Gendler | |
| 5,475,052 | A | 12/1995 | Rhee et al. | |
| 5,478,739 | A | 12/1995 | Slivka et al. | |
| 5,484,601 | A | 1/1996 | O'Leary et al. | 424/422 |
| 5,510,121 | A | 4/1996 | Rhee et al. | |
| 5,514,180 | A | 5/1996 | Heggeness et al. | |
| 5,516,532 | A | 5/1996 | Atala et al. | 424/548 |
| 5,543,392 | A | 8/1996 | Tomita et al. | |
| 5,545,229 | A | 8/1996 | Parsons et al. | |
| 5,562,736 | A | 10/1996 | Ray et al. | |
| 5,563,124 | A | 10/1996 | Damien et al. | 514/21 |
| 5,591,234 | A | 1/1997 | Kirsch | |
| 5,595,722 | A | 1/1997 | Grainger et al. | |
| 5,616,490 | A | 4/1997 | Sullivan et al. | |
| 5,629,009 | A | 5/1997 | Laurencin et al. | |
| 5,632,747 | A | 5/1997 | Scarborough et al. | |
| 5,645,597 | A | 7/1997 | Krapiva | |
| 5,656,492 | A | 8/1997 | Glowacki et al. | |
| 5,656,587 | A | 8/1997 | Sporn et al. | |
| 5,658,343 | A | 8/1997 | Hauselmann et al. | |
| 5,658,882 | A | 8/1997 | Celeste et al. | |
| 5,681,310 | A | 10/1997 | Yuan et al. | |
| 5,681,353 | A | 10/1997 | Li et al. | |
| 5,705,477 | A | 1/1998 | Sporn et al. | |
| 5,707,962 | A | 1/1998 | Chen et al. | |
| 5,716,416 | A | 2/1998 | Lin | |
| 5,718,707 | A | 2/1998 | Mikhail | |
| 5,723,331 | A | 3/1998 | Tubo et al. | |
| 5,741,685 | A | 4/1998 | Vacanti | |
| 5,786,217 | A | 7/1998 | Tubo et al. | |
| 5,800,537 | A | 9/1998 | Bell | |
| 5,817,153 | A | 10/1998 | Pendl et al. | |
| 5,821,333 | A | 10/1998 | Carter et al. | |
| 5,824,093 | A | 10/1998 | Ray et al. | |
| 5,827,328 | A | 10/1998 | Buttermann | |
| 5,830,859 | A | 11/1998 | Schmidt | 514/12 |
| 5,842,477 | A | 12/1998 | Naughton et al. | |
| 5,854,397 | A | 12/1998 | Mechanic et al. | |
| 5,865,846 | A | 2/1999 | Bryan et al. | |
| 5,902,785 | A | 5/1999 | Hattersley et al. | |
| 5,904,716 | A | 5/1999 | Gendler | |
| 5,908,784 | A | 6/1999 | Johnstone et al. | |
| 5,919,235 | A | 7/1999 | Husson et al. | |
| 5,928,940 | A | 7/1999 | Sampath et al. | |
| 5,928,945 | A | 7/1999 | Seliktar et al. | |
| 5,944,754 | A | 8/1999 | Vacanti | |
| 5,962,325 | A | 10/1999 | Naughton et al. | |
| 5,962,405 | A | 10/1999 | Seelich | |
| 5,964,807 | A | 10/1999 | Gan et al. | |
| 5,968,556 | A | 10/1999 | Atala et al. | 424/548 |
| 5,972,884 | A | 10/1999 | Cohen et al. | |
| 5,976,186 | A | 11/1999 | Bao et al. | |
| 6,010,698 | A | 1/2000 | Kussendrager et al. | |
| 6,013,853 | A | 1/2000 | Athanasiou et al. | |
| 6,027,917 | A | 2/2000 | Celeste | |
| 6,027,919 | A | 2/2000 | Celeste et al. | |
| 6,034,062 | A | 3/2000 | Thies et al. | |
| 6,042,610 | A | 3/2000 | Li et al. | |
| 6,054,122 | A | 4/2000 | MacPhee et al. | |
| 6,080,579 | A | 6/2000 | Hanley et al. | |
| 6,118,043 | A | 9/2000 | Nies et al. | 623/16 |
| 6,120,760 | A | 9/2000 | Hotten et al. | 424/85.1 |
| 6,123,731 | A | 9/2000 | Boyce et al. | |
| 6,143,501 | A | 11/2000 | Sittinger et al. | |
| 6,150,163 | A | 11/2000 | McPherson et al. | |
| 6,150,328 | A | 11/2000 | Wang et al. | |
| 6,162,241 | A | 12/2000 | Coury et al. | |
| 6,177,406 | B1 | 1/2001 | Wang et al. | |
| 6,179,871 | B1 | 1/2001 | Halpern | |
| 6,180,605 | B1 | 1/2001 | Chen et al. | 514/12 |
| 6,187,742 | B1 | 2/2001 | Wozney et al. | |
| 6,206,923 | B1 | 3/2001 | Boyd et al. | |
| 6,211,157 | B1 | 4/2001 | Benedict et al. | |
| 6,242,247 | B1 | 6/2001 | Reiser et al. | |
| 6,245,107 | B1 | 6/2001 | Ferree | |
| 6,251,143 | B1 | 6/2001 | Schwartz et al. | |
| 6,294,656 | B1 | 9/2001 | Mittl et al. | |
| 6,299,650 | B1 | 10/2001 | Van Blitterswijk et al. | |
| 6,305,379 | B1 | 10/2001 | Wolfinbarger, Jr. | 128/898 |
| 6,315,992 | B1 | 11/2001 | Noh et al. | |
| 6,340,369 | B1 | 1/2002 | Ferree | |
| 6,344,058 | B1 | 2/2002 | Ferree | |
| 6,352,557 | B1 | 3/2002 | Ferree | |
| 6,372,257 | B1 | 4/2002 | Marchosky | |
| 6,413,511 | B1 | 7/2002 | Glorioso et al. | |
| 6,419,702 | B1 | 7/2002 | Ferree | |
| 6,429,013 | B1 | 8/2002 | Halvorsen et al. | |
| 6,451,060 | B2 | 9/2002 | Masuda et al. | |
| 6,468,960 | B1 | 10/2002 | Lukanidin et al. | |
| 6,492,327 | B2 | 12/2002 | Junker et al. | |
| 6,498,142 | B1 | 12/2002 | Sampath et al. | |
| 6,511,958 | B1 | 1/2003 | Atkinson et al. | 514/2 |
| 6,514,514 | B1 | 2/2003 | Atkinson et al. | 424/423 |
| 6,534,095 | B1 | 3/2003 | Moore-Smith et al. | 424/549 |
| 6,558,949 | B2 | 5/2003 | Min et al. | |
| 6,559,119 | B1 | 5/2003 | Burgess et al. | |
| 6,582,471 | B1 | 6/2003 | Bittmann et al. | |
| 6,582,960 | B1 | 6/2003 | Martin et al. | |
| 6,626,945 | B2 | 9/2003 | Simon et al. | |
| 6,626,950 | B2 | 9/2003 | Brown et al. | |

(56) References Cited

U.S. PATENT DOCUMENTS

| | | | |
|---|---|---|---|
| 6,627,230 B2 | 9/2003 | Benedict et al. | 424/549 |
| 6,649,168 B2 | 11/2003 | Arvinte et al. | |
| 6,723,335 B1 | 4/2004 | Moehlenbruck et al. | |
| 6,833,408 B2 | 12/2004 | Sehl et al. | |
| 6,992,066 B2 | 1/2006 | Akella et al. | |
| 7,081,240 B1 | 7/2006 | Akella et al. | |
| 7,083,964 B2 | 8/2006 | Kurfurst | |
| 7,087,227 B2 | 8/2006 | Adkisson | |
| 7,087,577 B2 | 8/2006 | Benedict et al. | |
| 7,122,057 B2 * | 10/2006 | Beam et al. | 623/23.51 |
| 7,132,110 B2 | 11/2006 | Kay et al. | |
| 7,141,072 B2 | 11/2006 | Geistlich et al. | |
| 7,141,262 B2 | 11/2006 | Maubois et al. | |
| 7,235,255 B2 | 6/2007 | Austin et al. | |
| 7,238,678 B2 | 7/2007 | Elson et al. | |
| 7,241,874 B2 * | 7/2007 | Thorne | 530/412 |
| 7,273,756 B2 | 9/2007 | Adkisson et al. | |
| 7,341,999 B2 | 3/2008 | Akella et al. | 514/21 |
| 7,622,562 B2 * | 11/2009 | Thorne et al. | 530/350 |
| RE41,286 E | 4/2010 | Atkinson et al. | |
| 7,847,072 B2 * | 12/2010 | Thorne | 530/412 |
| 2001/0007023 A1 | 7/2001 | Lough, Jr. et al. | 530/841 |
| 2001/0041792 A1 | 11/2001 | Donda et al. | 530/399 |
| 2002/0009789 A1 | 1/2002 | Hanyu et al. | |
| 2002/0013627 A1 | 1/2002 | Geistlich et al. | |
| 2002/0040004 A1 | 4/2002 | Benedict et al. | |
| 2002/0173453 A1 | 11/2002 | Akella et al. | 514/12 |
| 2003/0135209 A1 | 7/2003 | Seedhom et al. | |
| 2003/0153078 A1 | 8/2003 | Libera et al. | |
| 2003/0176345 A1 | 9/2003 | Dawson | 514/12 |
| 2004/0033212 A1 | 2/2004 | Thomson et al. | |
| 2004/0072322 A1 | 4/2004 | Thorne | 435/226 |
| 2004/0081704 A1 | 4/2004 | Benedict et al. | |
| 2005/0026133 A1 | 2/2005 | Nakatsuji et al. | |
| 2005/0064041 A1 | 3/2005 | O'Leary et al. | 424/549 |
| 2005/0096274 A1 | 5/2005 | Lough et al. | 514/12 |
| 2005/0152882 A1 | 7/2005 | Kizer et al. | |
| 2005/0175657 A1 | 8/2005 | Hunter et al. | |
| 2005/0186247 A1 | 8/2005 | Hunter | |
| 2005/0196387 A1 | 9/2005 | Seyedin et al. | |
| 2005/0265980 A1 | 12/2005 | Chen et al. | |
| 2006/0008530 A1 | 1/2006 | Seyedin et al. | |
| 2006/0024373 A1 | 2/2006 | Shahar et al. | |
| 2006/0057184 A1 | 3/2006 | Nycz et al. | 424/426 |
| 2006/0128016 A1 | 6/2006 | Tokushima et al. | |
| 2006/0228391 A1 | 10/2006 | Seyedin et al. | |
| 2006/0240064 A9 | 10/2006 | Hunter et al. | |
| 2006/0251631 A1 | 11/2006 | Adkisson, IV et al. | |
| 2006/0275273 A1 | 12/2006 | Seyedin et al. | |
| 2006/0286157 A1 | 12/2006 | Akella et al. | 424/445 |
| 2007/0049731 A1 | 3/2007 | Thorne et al. | |
| 2007/0066525 A1 | 3/2007 | Lee et al. | 514/12 |
| 2007/0077236 A1 | 4/2007 | Osther | |
| 2007/0087032 A1 | 4/2007 | Chang et al. | |
| 2007/0128155 A1 | 6/2007 | Seyedin et al. | |
| 2007/0212389 A1 | 9/2007 | Weiss et al. | |
| 2008/0081369 A1 | 4/2008 | Adkisson, IV et al. | |

FOREIGN PATENT DOCUMENTS

| | | |
|---|---|---|
| CA | 2330665 A1 | 11/1999 |
| CN | 1163780 A | 10/1997 |
| DE | 2933174 A1 | 4/1980 |
| DE | 4306661 A1 | 9/1994 |
| DE | 4317448 A1 | 11/1994 |
| DE | 19503504 A1 | 3/1996 |
| DE | 19925519 A1 | 12/2000 |
| DE | 69714035 T2 | 3/2003 |
| EP | 0121976 A2 | 10/1984 |
| EP | 0312208 A1 | 4/1989 |
| EP | 0339607 A2 | 11/1989 |
| EP | 0171176 B1 | 2/1991 |
| EP | 0411925 A2 | 2/1991 |
| EP | 0493698 A1 | 7/1992 |
| EP | 0 243 179 B1 | 10/1992 |
| EP | 0516901 A1 | 12/1992 |
| EP | 0339607 B1 | 2/1993 |
| EP | 0469070 B1 | 9/1996 |
| EP | 0747066 A2 | 12/1996 |
| EP | 0768332 A1 | 4/1997 |
| EP | 0896825 A1 | 2/1999 |
| EP | 0433225 B1 | 4/1999 |
| EP | 0896825 B1 | 7/2002 |
| EP | 0747066 B1 | 12/2003 |
| GB | 1224925 | 3/1971 |
| GB | 2137209 A | 10/1984 |
| JP | 59190919 A | 10/1984 |
| JP | 60226814 A | 11/1985 |
| JP | 6136223 A | 2/1986 |
| JP | 62255429 A | 11/1987 |
| JP | 1265968 A | 10/1989 |
| JP | 29394 A | 1/1990 |
| JP | 211599 A | 1/1990 |
| JP | 2156954 A | 6/1990 |
| JP | 3503649 | 8/1991 |
| JP | 3505098 | 11/1991 |
| JP | 5501208 A | 3/1993 |
| JP | 5505305 A | 3/1993 |
| JP | 5505404 A | 8/1993 |
| JP | 6505258 A | 6/1994 |
| JP | 6507173 A | 8/1994 |
| JP | 9505305 A | 5/1997 |
| JP | 10167980 A | 6/1998 |
| JP | 11507697 | 7/1999 |
| JP | 2001514935 A | 9/2001 |
| JP | 2001519700 T | 10/2001 |
| WO | WO88/03409 | 5/1988 |
| WO | WO-9012603 A1 | 11/1990 |
| WO | WO-9116867 A1 | 11/1991 |
| WO | WO-9209697 A1 | 6/1992 |
| WO | WO-9214481 A1 | 9/1992 |
| WO | WO 92/18142 | 10/1992 |
| WO | WO-9315694 A1 | 8/1993 |
| WO | WO-9409722 A1 | 5/1994 |
| WO | WO-9420151 A1 | 9/1994 |
| WO | WO-9425080 A1 | 11/1994 |
| WO | WO-9426211 A1 | 11/1994 |
| WO | WO-9426322 A1 | 11/1994 |
| WO | WO-9513767 A1 | 5/1995 |
| WO | WO-9516035 A2 | 6/1995 |
| WO | WO-9530383 A1 | 11/1995 |
| WO | WO-9602733 A1 | 2/1996 |
| WO | WO-9603112 A1 | 2/1996 |
| WO | WO-9624302 A1 | 8/1996 |
| WO | WO-9624310 A1 | 8/1996 |
| WO | WO-9627333 A1 | 9/1996 |
| WO | WO-9634955 A1 | 11/1996 |
| WO | WO-9639169 A1 | 12/1996 |
| WO | WO-9639170 A1 | 12/1996 |
| WO | WO-9641818 A1 | 12/1996 |
| WO | WO-9730662 A1 | 8/1997 |
| WO | WO-9738676 A1 | 10/1997 |
| WO | WO-9741880 A1 | 11/1997 |
| WO | WO-9746665 A1 | 12/1997 |
| WO | WO-9804681 A2 | 2/1998 |
| WO | WO-9822492 A1 | 5/1998 |
| WO | WO-9832333 A1 | 7/1998 |
| WO | WO-9835653 A1 | 8/1998 |
| WO | WO-9844874 A1 | 10/1998 |
| WO | WO-9856317 A1 | 12/1998 |
| WO | WO-9902674 A1 | 1/1999 |
| WO | WO-9908728 A1 | 2/1999 |
| WO | WO-9931136 A1 | 6/1999 |
| WO | WO-9931136 A2 | 6/1999 |
| WO | WO 99/55395 | 11/1999 |
| WO | WO-9955395 A1 | 11/1999 |
| WO | WO-9957146 A1 | 11/1999 |
| WO | WO-0015274 A1 | 3/2000 |
| WO | WO-0017321 A1 | 3/2000 |
| WO | WO-0048550 A2 | 8/2000 |
| WO | WO-0062832 A1 | 10/2000 |
| WO | WO-0134166 A1 | 5/2001 |
| WO | WO-0143667 A1 | 6/2001 |

(56) References Cited

FOREIGN PATENT DOCUMENTS

| WO | WO01/66130 | 9/2001 |
|---|---|---|
| WO | WO-0166130 A1 | 9/2001 |
| WO | WO-0168811 A2 | 9/2001 |
| WO | WO-0168811 A3 | 9/2001 |
| WO | WO-0176654 A1 | 10/2001 |
| WO | WO-0185225 A2 | 11/2001 |
| WO | WO02/00244 | 1/2002 |
| WO | WO-0200244 A2 | 1/2002 |
| WO | WO 02/44380 | 6/2002 |
| WO | WO02/47713 | 6/2002 |
| WO | WO-0244380 A2 | 6/2002 |
| WO | WO-0247713 A2 | 6/2002 |
| WO | WO-0247713 A3 | 6/2002 |
| WO | WO-0250112 A2 | 6/2002 |
| WO | WO-0250112 A3 | 6/2002 |
| WO | WO 03/004990 | 1/2003 |
| WO | WO-03004990 A2 | 1/2003 |
| WO | WO-03026689 A1 | 4/2003 |
| WO | WO-0360076 A2 | 7/2003 |
| WO | WO-0360076 A3 | 7/2003 |
| WO | WO-03059436 A2 | 7/2003 |
| WO | WO-03077852 A2 | 9/2003 |
| WO | WO-200747066 B1 | 12/2003 |
| WO | WO-2004075940 A1 | 9/2004 |
| WO | WO2005/084701 | 9/2005 |
| WO | WO2006/093545 | 9/2006 |
| WO | WO-2007011610 A2 | 1/2007 |
| WO | WO2007/053850 | 5/2007 |
| WO | WO-0285422 A1 | 10/2008 |
| WO | WO-2009073106 A1 | 6/2009 |

OTHER PUBLICATIONS

Li, Biologic Biomaterials: Tissue-Derived Biomaterials (Collagen), CRC Press, Inc., pp. 627-647 (1995).
Mueller, et al, "Myocardial Angiogenesis Induction With Bone Protein Derived Growth Factors (Animal Experiment)," Swiss Medical Weekly 131:23-25 (2001).
Nakaoka, et al, "Inhibition of Rat Vascular Smooth Muscle Proliferation In Vitro and In Vivo by Bone Morphogenetic Protein-2," Journal of Clinical Investigation 100(111:2824-2832 (1997).
Nakashima, et al, "The Novel Zinc Finger—Containing Transcription Factor Osterix is Required for Osteoblast Differentiation and Bone Formation," Cell Press 108:17-29 (2002).
Ogawa, et al, "Purification of Transforming Growth Factors β1 and β2 from Bovine Bone and Cell Culture Assays," Methods of Enzymology 198:317-327 (1991).
Rodeo, et al, "Use of Recombinant Human Bone Morphogenetic Protein-2 to Enhance Tendon Healing in a Bone Tunnel," The American Journal of Sports Medicine 27(4):476-488 (1999).
Schumacher, et al, "Induction of Neoangiogenesis in Ischemic Myocardium by Human Growth Factors," Clinical Investigation and Reports 97:645-650 (1998).
Seyedin, et al, "Purification and Characterization of Two Cartilage-Inducing Factors from Bovine Demineralized Bone," Proc. Natl. Acad. Sci. 82:2267-2271 (1985).
Vukicevic, et al., "Osteogenic Protein-1 (Bone Morphogenetic Protein-7) Reduces Severity of Injury After Ischemic Acute Renal Failure in Rat," Journal of Clinical Evaluation 1020:202-214 (1998).
Wolfinbarger, et al., "Demineralized Bone Matrix: Maximizing New Bone Formation for Successful Bone Implantation," Orthopedic Biology and Medicine: Musculoskeletal Tissue Regeneration, Biological Materials and Methods, pp. 93-117 (2002).
Yamashita, et al, "Growth/Differentiation Factor-5 induces Angiogenesis In Vivo," Experimental Cell Research, 235:218-226 (1997).
Han et al., "Quantitative and sensitive in vitro assay for osteoinductive activity of demineralized bone matrix," Journal of Orthopaedic Research 21:648-654 (2003).
Zhou et al., "Comparison of TGF-β/BMP Pathways Signaled by Demineralized Bone Powder and BMP-2 in Human Dermal Fibroblasts," Journal of Bone and Mineral Research 19(10):1732-1741 (2004).

Judy Glowacki, "A review of osteoinductive testing methods and sterilization processes for demineralized bone," Cell and Tissue Banking 6:3-12 (2005).
Aguiar, Dean, et al., "Notochordal Cells Interact with Nucleus Pulposus Cells: Regulation of Proteoglycan Synthesis", Exp. Cell. Res. vol. 246, (1999), 129-137.
Ahlgren, et al., "Effect of Anular Repair on the Healing Strength of the Intervertebral Disc", Spine vol. 25, (2000), 2165-2170.
Alini, M, et al., "A biological approach to treating disc degeneration: Not for today, but maybe for tomorrow", Eur. Spine J. vol. 11 (2), XP002287478 ISSN: 0940-6719, (2002), S215-S220.
Alpasian, C., et al., "Long-term evaluation of recombinant human bone morphogenic protein-2 induced bone formation with a biologic and synthetic delivery system", British Journal of Oral and Maxofacial Surgery, 34, (1996), 414-418.
Antoniou, et al., "The Human Lumbar Intervertebral Disc", J. Clin. Invest. 98, (Aug. 1996), 996-1003.
Antoniou, J, et al., "The Human Lumbar Endplate: Evidence of Changes in Biosynthesis and Denaturation of the Extracellular Matrix with Growth, Maturation, Aging, and Degeneration", Spine vol. 21, No. 10, (May 15, 1996), 1153-1161.
Ariga, Kenta, et al., "The Relationship Between Apoptosis of Endplate Chondrocytes and Aging and Degeneration of the Intervertebral Disc", Spine vol. 26, No. 22, (2001), 2414-2420.
Arnoczky, S. P., et al., "Building a Meniscus: Biologic Considerations", Clinical Orthopaedics and Related Research No. 367S, (Oct. 1999), S244-S253.
Aston, Jayne E, et al., "Repair of Articular Surfaces by Allografts of Articular and Growth-Plate Cartilage", vol. 68-B, No. I, British Editorial Society of Bone and Joint Surgery, England, (1986), 29-35.
Atkinson, et al., "Elucidation of Homeoprotein Cart-1 Function During In Vitro Chondrogenesis of C3H10T1/2 Micromass Cultures", Annals New York Academy of Sciences, 785, (Jun. 1996), 206-208.
Atkinson, B. L., et al., "A Combination of Osteoinductive Proteins Induces Type II Collagen Production in Adult Myoblast and Dermal Cells", 44th Annual Meeting, Orthopaedic Research Society, New Orleans, Louisiana, (Mar. 16-19, 1998), p. 889.
Atkinson, B. L., et al., "Combination of Osteoinductive Bone Proteins Differentiates Mesenchymal C2H/10T1/2 Cells Specifically to the Cartilage Lineage", Journal of Cellular Biochemistry 65, (1997), 325-339.
Aulthouse, Amy Lynn, et al., "Expression of the Human Chondrocyte Phenotype in Vitro", vol. 25, No. 7, In Vitro Cellular & Developmental Biology, USA, (1989), 659-668.
Azizkhan, et al., "Chondrocytes contain a growth factor that is localized in the nucleus and is associated with chomatin", Proc. Natl. Acad. Sci., vol. 77, No. 5, (1980), 2762-2766.
Bacsich, P, et al., "The Significance of the Mucoprotein Content on the Survival of Homografts of Cartilage and Cornea", vol. LXII, Part III, P.R.S.E., USA, (1946), 321-327.
Bakay, et al., "A mushroom-shaped osteochondral patella allograft", International Orthopaedics (SICOT) 20, (1996), 370-372.
Bakay, et al., "Osteochondral resurfacing of the knee joint with allograft", International Orthopaedics (SICOT) 22, (1998), 277-281.
Bao, Qi-Bin, et al., "The artificial disc: theory, design and materials", Biomaterials 17, (1996), 1157-1167.
Baragi, et al., "Transplantation of adenvirally transduced allogeneic chondrocytes into articular cartilage defects in vivo", Osteoarthritis and cartilage, vol. 5, (1997), 275-282.
Barry, et al., "Chondrogenic Constructs of Mesenchymal Stem Cells on Hyaff-II, A Hyaluronan Ester, as Implants for Repair of Osteochondral Lesions", 44th Annual Meeting, Orthopaedic Research Society, New Orleans, Louisiana, (Mar. 16-19, 1998), 799.
Bassleer, C, et al., "Human Chondrocytes in Tridimensional Culture", vol. 22, No. 3, PI. 1, In Vitro Cellular & Developmental Biology, UK, (1986), 113-119.
Bentz, Hanne, et al., "Transforming Growth Factor-β2 Enhances the Osteo-inductive Activity of a Bovine Bone-Derived Fraction Containing Bone Morphogenetic Protein-2 and 3", Matrix, vol. 11, (1991), 269-279.
Binette, F, et al., "Tenninally Redifferentiated Human Articular Chondrocytes Express Hyaline Cartilage Markers without

(56) References Cited

OTHER PUBLICATIONS

Hypertrophy", Genzyrne Tissue Repair, 43rd Annual Meeting, Orthopaedic Research Society, USA, (520), 1997.
Blanco, M. D., et al., "Development and characterization of protein-loaded poly (lactide-co-glycolide) nanospheres", European Journal of Pharmaceuticals and Biopharmaceutics, 43(3), (1997), 287-294.
Block, et al., "Glycol Methacrylate Embedding Technique Emphasizing Cost Containment, Ultrarapid Processing, and Adaptability to a Variety of Staining Techniques", Laboratory medicine 13(5), (May 1982), 290-298.
Boden, S. D., et al., "In Vivo Evaluation of a Resorbable Osteoinductive Composite as a Graft Substitute for Lumbar Spinal Fusion", Journal of Spinal Disorders 10(1), (1997), 1-11.
Boumediene, et al., "Modulation of rabbit articular chondrocyte (RAC) proliferation by TGF-B isoforms", Cell Prolif., vol. 28, (1995), 221-234.
Bourque, William, et al., "Expression of four growth factors during fracture repair", Int. J. Dev. Bioi. 37, (1993), 573-579.
Bram, "Expression of PTHrP, Indian Hedgehoge and their receptors in the posinatel rat growth plates evidence for a locally acting growth restraining feedback loop", ASBMR 21st Annual Meeting, Abstract, (2000), 1 pg.
Bruns, et al., "Perichondrium trnsplatation bei Gelenkknorpelschaden", IW Sport + Medizin, vol. 9, No. 2, (1997), 90-94.
Buckwalter, J A, "Spine Update: Aging and Degeneration of the Human Intervertebral Disc", Spine 20, (Jun. 1, 1995), 1307-1314.
Buckwalter, J A, "Spine Update: Aging and Degeneration of the Human Intervertebral Disk", Spine vol. 20, No. 11, (Jun. 1, 1995), 1307-1314.
Bujia, et al., "Synthesis of human cartilage using organotypic cell culture", ORL, vol. 55, (1993), 347-351.
Bujia, J, et al., "Effect of Growth Factors on Cell Proliferation by Human Nasal Septal Chondrocytes Cultured in Monolayer", Acta Otolaryngol, vol. 114, Scandinavian University Press, Sweden, (539-543), 1994.
Bulpitt, et al., "New strategy for chemical modification of hyaluronic acid: Preparation of functionalized derivatives and their use in the formation of novel biocompatible hydrogels", In Situ Polymerizable Hyaluronic Acid Hydrogel Materials, (1999), 152-169.
Chelberg, Mary, et al., "Identification of hetergeneous cell populations in normal human intervertebral disc", J. Anat. 186, (1995), 43-53.
Chen, et al., "Streaming potentials during the confined compression creep test of normal and proteoglycan-depleted cartilage", Ann. Biomed. Eng. 25, (Mar. 1997), 269-277.
Chernousov, Michael, et al., "Role of the I-9 and III-1 Modules of Fibronectin in Formation of an Extracellular Fibronectin Matrix", The Journal of Biological Chemistry 266 (17), (1991), 10851-10858.
Chiba, Kazuhiro, et al., "A New Culture System to Study to the Metabolism of the Intervertebral Disc In Vitro", Spine 23, (1998), 1821-1827.
Cinotti, G, et al., "Results of Disc Prosthesis After a Minimum Follow-Up Period of 2 years", Spine 21, (Apr. 15, 1996), 995-1000.
Cornell, et al., "A biosensor that uses ion-channel switches", Nature vol. 387, (Jun. 1997), 580-583.
Cuevas, et al., "Fibroblast Growth Factor Protects the Kidney Against Ischemia-Reperfusion Injury", European Journal of Medical Research vol. 4, (Oct. 15, 1999), 403-410.
Czitrom, et al., "Bone and Cartilage Allotransplantation: Review of 14 Years of Research and Clinical Studies", Clinical Orthopedics and Related Research, (1986), 141-145.
Damien, C. J., et al., "A Composite of Natural Coral, Collagen, Bone Protein and Basic Fibroblast Growth Factor Tested in a Rat Subcutaneous Model", Annales Chirugiae et Gynaecologiae Suppl, 207, (1993), 117-128.
De Groot, J H, et al., "Meniscal tissue regeneration in porous 50/50 copoly (L-lactide/E-caprolactone) implants", Biomaterials 18 (8), (1997), 613-622.

Delbruck, Axel, et al., "In-Vitro Culture of Human Chondrocytes from Adult Subjects", Connective Tissue Research, Gordon and Breach, Science Publishers, Inc., USA, (1986), 155-172.
Delloye, et al., "Osteochondral Allografts in Arm and Forearm Surgery", Acta Orthopaedica Belgica, vol. 57, (1991), 75-83.
Denker, et al., "Formation of cartilage-like spheroids by micromass cultures of murine C3H10T1/2 cells upon treatment with transforming growth factor-beta1", Differentiation 59, (1995), 25-34.
Duance, Victor, et al., "Changes in Collagen Cross-Linking in Degenerative Disc Disease and Scoliosis", Spine 23, (1998), 2545-2551.
Duggirala, S. S., et al., "Interaction of Recombinant Human Bone Morphogenic Protein-2 with Poly (d,l, Lactide-co-glycolide) Microspheres", Pharmaceutical and Development and Technology, 1(1), (1996), 11-19.
Duggirala, S. S., et al., "The Evaluation of Lyophilized Polymer Matrices for Administering Recombinant Human Bone Morphogenic Protein-2", Pharmaceutical Development and Technology 1(2), (1996), 165-174.
Elima, Kati, et al., "Expression of mRNAs for collagens and other matrix components in dedifferentiating and redifferentiating human chondrocytes in culture", FEBS Letters, vol. 258 No. 2, Elsevier Science Publishers B.V. (Biomedical Division), UK, (1989), 195-198.
Enker, P, et al., "Artificial Disc Replacement: Preliminary Report with a 3-Year Minimum Follow-Up", Spine 18, (1061-1070), Jun. 15, 1993.
Ertl, W., et al., "Successful Meniscal Repair Utilizing Meniscal Tissue Engineered Constructs: One Year Results", Trans. Orthop. Res. Soc., 21, (42nd Annual Meeting, Orthopaedic Research Society, Atlanta Georgia, Feb. 19-22, 1996), (1996), p. 539.
Fithian, Donald, et al., "Material Properties and Structure—Function Relationships in the Menisci", Clinical Orthopedics vol. 252, (Mar. 1990), 19-31.
Flynn, et al., "Osteoarticular Allografts to Treat Distal Femoral Osteonecrosis", Clinical Orthopaedics and Related Research, 303, (1994), 38-43.
Freed, L E, et al., "Neocartilage formation in virtro and invivo using cells cultured on synthetic biodegradable polymers", J. Biomed. Mater. Res. vol. 27 (1), (1993), 11-23.
Freed, L. E., et al., "Cartilage Tissue Engineering Based on Cell-Polymer Constructs", Tissue Engineering of Cartilage, CRC Press, Inc., USA, (1995), 1788-1806.
Freed, L. E., et al., "Composition of Cell-Polymer Cartilage Implants", Biotechnology and Bioengineering, vol. 43, John Wiley & Sons, Inc., USA, (1994), 605-614.
Freed, L. E., et al., "Cultivation of Cell-Polymer Cartilage Implants in Bioreactors", Journal of Cellular Biochemistry, vol. 51, Wiley-Liss, Inc., USA, (1993), 257-264.
Freed, L. E., et al., "Cultivation of Cell-Polymer Tissue Constructs in Simulated Microgravity", Biotechnology and Bioengineering, vol. 46, John Wiley & Sons, Inc., USA, (1995), 306-313.
Freed, L. E., et al., "Neocartilage formation in vitro and in vivo using cells cultured on synthetic biodegradable polymers", Journal of Biomedical Materials Research, vol. 27, John Wiley & Sons, Inc., USA, (1993), 11-23.
Frick, S L, et al., "Lumbar Intervertebral Disc Transfer: A Canine Study", Spine vol. 19, (Aug. 15, 1994), 1826-1834.
Fu?, M, et al., "Characteristics of human chondrocytes, osteoblasts and fibroblasts seeded onto a type I/II collagen sponge under different culture conditions", Annals of Anatomy, vol. 182, Urban & Fischer Verlag, Germany, (2000), 303-310.
Galera, et al., "Effect of transforming growth factor-B1 (TGF-B1) on matrix synthesis by monolayer cultures of rabbit chondrocytes during the dedifferentiating process", Experimental Cell Research, vol. 200, (1992), 379-392.
Garrett, John C, "Fresh Osteochondral Allografts for Treatment of Articular Defects in Osteochondritis Dissecans of the Lateral Femoral Condyle in Adults", Clinical Orthopaedics and Related Research, 303, (1994), 33-37.
Griffith, S L, et al., "A Multicenter Retrospective Study if the Clinical Results fo the LINK SB Charite Intervertebral Prosthesis: The Initial European Experience", Spine vol. 19, (Aug. 15, 1994), 1842-1849.

(56) References Cited

OTHER PUBLICATIONS

Gross, "Use of Fresh Osteochondral Allografts to Replace Traumatic Joint Defects", Allografts in Orthopaedic Practice, (1992), 67-82.

Gruber, Helen, et al., "Anti-Apoptotic Effects of IGF-1 and PDGF on Human Intervertebral Disc Cells In Vitro", Spine vol. 25, No. 17, (2000), 2153-2157.

Gu, et al., "The Anisotropic Hydraulic Permeability of Human Lumbar Anulus Fibrosus: Influence of Age, Degeneration, Direction and Water Content", Spine vol. 24, (1999), 2449-2455.

Guerne, et al., "Growth Factor Responsiveness of Human Articular Chondrocytes: Distinct Profiles in Primary Chondrocytes, subcultured chondrocytes, and Fibroblasts", The Journal of Cellular Physiology 158, (1994), 476-484.

Guerne, et al., "IL-6 Production by Human Articular Chondrocytes: Modulation on its Synthesis by Cytokines, Growth Factors, and Hormones in Vitro", The Journal of Immunology 144, (Jan. 15, 1990), 499-505.

Guerne, P., et al., "Growth factor responsiveness of human articular chondrocytes in aging and development", Arthritis and Rheumatism 38(7), (Jul. 1995), 960-968.

Haart, et al., "Optimization of chondrocyte expansion in culture", Acta Orthop Scand, vol. 70, No. 1, (1999), 55-61.

Hadjipavlou, Alexander, et al., "The Effect of Chymopapain on Low Back Pain", Orthopaedic Review vol. 21, No. 6, (Jun. 1992), 733-738.

Harrison, et al., "Osteogenin promotes reexpression of cartilage phenotype by dedifferentiated articular chondrocytes in serum-free medium", Experimental Cell Research, vol. 192, (1991), 340-345.

Harrison, et al., "Transforming growth factor-beta: Its effect on phenotype reexpression by dedifferentiated chondrocytes in the presence and absence of osteogenin", In Vitro Cell Dev. Biol., vol. 28A, (1992), 445-448.

Hashimoto, Jun, et al., "Meniscal repair using fibrin sealant and endothelial cell growth factor", Amer. J. Sports Med. vol. 20 (5), (1992), 537-541.

Hill, et al., "The purification and partial characterization of bone resorptive polypeptides from bovine bone matrix", Biochimica et Biophysica Acta vol. 1201, (1994), 193-202.

Hiraki, et al., "Effect of transforming growth factor B on cell proliferation and glycosaminoglycen synthesis by rabbit growth-plate chondrocytes in culture", Biochimica et Biophysica Acta, vol. 969, (1988), 91-99.

Hiraki, Yuji, et al., "Bone Morphogenetic Proteins (BMP-2 and BMP-3) Promote Growth and Expression of the Differentiated Phenotype of Rabbit Chondrocytes and Osteoblasic MC3T3-E1 Cells in Vitro", Journal of Bone and Mineral Research 6 (12), (1991), 1373-1385.

Hollinger, Jeffrey O., et al., "Poly(alpha-hydroxy acids): carriers for bon morphogenetic proteins", Biomaterial, vol. 17, (1996), 187-194.

Horner, Heather, et al., "2001 Volvo Award Winner in Basic Science Studies: Effect of Nutrient Supply on the Viability of Cells From the Nucleus Pulposus of the Intervertebral Disc", Spine vol. 26, (2001), 2543-2549.

Horton, et al., "Transforming growth factor-beta and fibroblast growth factor act synergistically to inhibit collagen II synthesis through a mechanism involving regulatory DNA sequences", Journal of Cellular Physiology, vol. 141, (1989), 8-15.

Hu, et al., "Injection of basic fibroblast growth factor and bone morphogenetic protein for osteogenesis stimulation", Chemical Abstracts 132 (4) Abstract No. 40522x, (Jan. 2000), 1132.

Hu, Zhenming, et al., "Role of Bovine Bone Morphogenetic Proteins in Bone Matrix Protein and Osteoblast-Related Gene Expression During Rat Bone Marrow Stromal Cell Differentiation", The Journal of Craniofacial Surgery, vol. 16, No. 6, (Nov. 2005), 11 pgs.

Ibarra, et al., "Transplantation of Tissue Engineered Meniscus in Sheep", 44th Annual Meeting, Orthopaedic Research Society, New Orleans, Louisiana, (Mar. 16-19, 1988), 293.

Ibarra, C, et al., "Tissue Engineered Menscus: A Potential New Alternative to Allogenic Meniscus Transplantation", Transplant. Proc. vol. 29, (1997), 986-988.

Ibarra, C., et al., "Tissue Engineered Repair of Canine Meniscus Explants in Vitro and in a Nude Mice Model", 44th Annual Meeting, Orthopaedic Research Society, New Orleans, Louisiana Mar. 16-19, 1998, (Mar. 1998), pp. 148-125.

Jahnke, Marianne, et al., "Proteoglycans of the human intervertebral disc", Biochem. J. vol. 251, (1988), 347-356.

Jaquiery, Claude, et al., "In Vitro Osteogenic Differentiation and In Vivo Bone-Forming Capacity of 8 Human Isogenic Jaw Periosteal Cells and Bone Marrow Stromal Cells", Annals of Surgery, vol. 242, No. 6, (Dec. 2005), 859-868.

Junchang, W. K., et al., "Percutaneous injection of bone morphogentic protein and polyvinyl pyrrolidone", Journal of Xi'an Medical University, 22(2), (w/ English Abstract), (Apr. 2001), 132-133.

Kaapa, E, et al., "Collagen Synthesis and Types I, III, IV, and VI Collagens in an Animal Model of Disc Degeneration", Spine vol. 20, (Jan. 1, 1995), 59-67.

Karner, Elerin, et al., "Differentiation of Human Embryonic Stem Cells Into Osteogenic or Hematopoietic Lineages: A Dose-Dependent Effect of Osterix Over- Expression", Journal of Cellular Physiology, vol. 218, No. 2., (Feb. 2009), 11 pgs.

Kawakami, M, et al., "Pathomechanism of Pain-related Behavior Produced by Allografts of Intervertebral Disc in the Rat", Spine vol. 21, (Sep. 15, 1996), 2101-2107.

Kawamura, et al., "Growth Factors, Mitogens, Cytokines, and Bone Morphogenetic Protein in Induced Chondrogenesis in Tissue Culture", Developmental Biology 130, (1988), 435-442.

Kawamura, et al., "Human Fibrin Is a Physiologic Delivery System for Bone Morphogenetic Protein", Clinical Orthopaedics and Related Research, (Oct. 1988), 302-310.

Kawa-Uchi, et al., "Fibroblast growth factor enhances expression of TGFB-stimulated—clone-22 gene in osteoblast-like cells", Endocrine, 3, (1995), 833-837.

Kempson, et al., "The tensile properties of the cartilage of human glycosaminoglycans", Biochem. Biophys. Acta., 297(2), (1973), 456-472.

Kenley, R., et al., "Osseous regeneration in the rat calvarium using novel delivery systems for recombination human bone morphogenic protein-2 (rhBMP-2)", Journal of Biomedical Materials Research, vol. 28, (1994), 1139-1147.

Kim, et al., "Differential Effects of Transforming Growth Factor-beta1 and Bone Morphogenetic Proteins in Cultured Rat Osteogenic Sarcoma and Mink Lung Epithelial Cells", Biochemistry and Molecular Biology International vol. 33, (May 1994), 253-261.

Kim, Young II, et al., "The antihypertensive effect of orally administered nifedipine-loaded nanoparticles in spontaneously hypertensive rats", Br J Pharmacol., 120(3), (Jan. 23, 1997), 399-404.

Klagsbrun, et al., "Purification of a cartilage-derived growth factor", The Journal of Biological Chemistry, vol. 255, No. 22, (1980), 10859-10866.

Klagsbrun, et al., "The stimulation of DNA synthesis and cell division in chondrocytes and 3T3 cells by a growth factor isolated from cartilage", Exp Cell Res, vol. 105, (1977), 99-108.

Kujawa, et al., "Hyaluronic acid bonded to cell culture surfaces inhibits the program of myogenesis", Developmental Biology, vol. 113, (1986), 10-16.

Kujawa, Mary J, et al., "Hyaluronic Acid Bonded to Cell-Culture Surfaces Timulates Chondrogenesis inStage 24 Limb Mesenchyme Cell Cultures", Developmental Biology, vol. 114, Academic Press, Inc., USA, (1986), 504-518.

Labhasetwar, Vinod, et al., "Nanoparticle drug delivery system for restenosis", Advanced Drug Delivery Reviews, vol. 24, (Feb. 1997), 63-85.

Lee, Joon, et al., "New Use of a Three-Dimensional Pellet Culture System for human Intervertebral Disc Cells", Spine vol. 26, No. 21, (2001), 2316-2322.

Levine, Jamie, et al., "Bone Morphogenetic Protein Promotes Vascularization and Osteoinduction in Preformed Hydroxyapatite in the Rabbit", Annals of Plastic Surgery vol. 39(2), (Aug. 1997), 158-168.

Liu, Lin-Shu, et al., "An osteoconductive collagen/hyaluronate matrix for bone regeneration", Biomaterials vol. 20, Elsevier, UK, (1999), 1097-1108.

(56) References Cited

OTHER PUBLICATIONS

Lucas, Paul A, et al., "Ectopic induction of cartilage and bone by water-soluble proteins from bovine bone using a collagenous delivery vehicle", Journal of Biomedical Materials Research: Applied Biomaterials, vol. 23, No. AI, John Wiley & Sons, Inc., USA, (1989), 23-39.
Luyten, Frank, et al., "Recombinant Bone Morphogenetic Protein-4, Transforming Growth Factor-Beta1, and Activin A Enhance the Cartilage Phenotype of Articular Chondrocytes in Vitro", Experimental Cell Research 210, (1994), 224-229.
MacKay, et al., "Chondrogenic differentiation of cultured human mesenchymal stem cells from marrow", Tissue Engineering, vol. 4, No. 4, (1998).
Madawi, A A, et al., "Biocompatible Osteoconductive Polymer Versus Iliac Graft: A Prospective Comparative Study for the Evaluation of Fusion Pattern After Anterior Cervical Discectomy", Spine vol. 21, (Sep. 15, 1996), 2123-2129.
Malemud, et al., "Bilogically erodible microsheres as potential oral drug delivery systems", Nature, vol. 386,, (1997), 410.
Martz, Erik, et al., "Materials and Design of Spinal Implants—A Review", Applied Biomaterials, (Sep. 1997), 267-288.
Mathiowitz, Edith, et al., "Biologically erodable microspheres as potential oral drug delivery systems", Nature, vol. 386, (Mar. 1997), 410-414.
Matsuzaki, H, et al., "Allografting Intervertebral Discs in Dogs: A Possible Clinical Application", Spine vol. 21, No. 2, (Jan. 15, 1996), 178-183.
McDevitt, Cahir, et al., "The Ultrastructure and Biochemistry of Meniscal Cartilage", Clinical Orthopedics, 252, (Mar. 1990), 8-18.
Meade, Karen, et al., "Immunogenicity of collagenous implants", Biomaterials vol. 11, (1990), 176-180.
Melrose, J, et al., "Proteoglycan Heterogeneity in the Normal Adult Ovine Intervertebral Disc", Matrix Biology vol. 14, (1994), 61-75.
Moore, et al., "Biocompatibility and Immunologic Properties of Pericardinal Tisue Stabilized by Dey-Mediated Photooxidation", J. Heart Valve Dis. vol. 6, (May 1997), 307-315.
Mow, V C, et al., "Experimental Studies on Repair of Large Osteochondral Defects at a High Weight Bearing Area of the Knee Joint: A Tissue Engineering Study", Transactions of the ASME, Journal of Biomechanical Engineering, vol. 113, USA, (1991), 198-207.
Nehrer, et al., "Autologous Chondrocyte-Seeded Type I and II Collagen Matrices Implanted in a Chondral Defect in a Canine Model", 44th Annual Meeting, Orthopaedic Research Society, New Orleans, Louisiana, (Mar. 16-19, 1998), 377.
Nehrer, et al., "Matrix collagen type and pore size influence behavior of seeded canine chondrocytes", Biomaterials, 18, (1997), 769-776.
Nimni, M E, "Polypeptide growth factor: targeted delivery systems", Biomaterials vol. 18, (Sep. 1997), 1201-1225.
Nishida, et al., "Adenovirus-Mediated Gene Transfer to Nucleus Pulposus Cells", Spine vol. 23, (1998), 2437-2442.
Nishida, et al., "Adenovirus-Mediated Gene Transfer to Nucleus Pulposus Cells", Spine, 24(23), (1999), 2419-2425.
Nishida, et al., "Modulation of the Biologic Activity of the Rabbit Intervertebral Disc by Gene Therapy: an In Vitro Study of Adenovirus-Mediated Transfer of the Human transforming Growth Factor B1 Encoding Gene", Spine 24, (1999), 2419-2425.
Nishimura, Kazuhiro, et al., "Percutaneous Reinsertion of the Nucleus Pulposus", Spine vol. 23, (1998), 1531-1538.
Nixon, Alan J, et al., "-laden porous collagen cartilage analogue", American Journal of Veterinary Research, vol. 54, No. 2, USA, (1993), 349-356.
Oegema, Theodore, et al., "Aggregated Proteoglycan Synthesis in Organ Cultures of Human Nucleus Pulposus", J. Biol. Chem. vol. 254, (1979), 10579-10581.
Ogawa, et al., "Bovine Bone Activin Enhances Bone Morphogenetic Protein-induced Ectopic Bone Formation", The Journal of Biological Chemistry vol. 267, (Jul. 15, 1992), 14233-14237.
Ogawa, et al., "Purification and Characterization of Transforming Growth Factor-beta2.3 and -beta1.2 Heterodimers from Bovine Bone", The Journal of Biological Chemistry vol. 267, (Feb. 5, 1992), 2325-2328.
Ogawa, et al., "Purification of Transforming Growth Factors-beta1 and -beta2 from Bovine Bone and Cell Culture Assays", Methods in Enzymology vol. 198, (1991), 317-327.
Okuma, Masahiko, et al., "Reinsertion of Stimulated Nucleus Pulposus Cells Retards Intervertebral Disc Degeneration: An In Vitro and In Vivo Experimental Study", J. Orthopaedic Research vol. 18, (2000), 988-997.
Olmarker, et al., "Ultrastructural Changes in Spinal nerve Roots Induced by Atuologous Nucleus Pulposus", Spine vol. 21, (Feb. 15, 1996), 411-414.
Pieter, A, et al., "Effect of purified growth factors on rabbit articular chondrocytes in monolayer culture", Arthritis and rheumatism, vol. 25, No. 10, (1982), 1217-1227.
Pokharna, Hemlata, et al., "Collagen Crosslinks in human Lumbar Intervertebral Disc Aging", Spine vol. 23, (1998), 1645-1648.
Pollok, et al., "Long term insulin-secretory function of islets of Langerhans encapsulated with a layer of confluent chondrocytes for immunoisolation", Pediatric Surg Int, vol. 15, (1999), 164-167.
Pollok, J. M., et al., "Immunoisolation of xenogeneic islets using a living tissue engineered cartilage barrier", Transplantation Proceedings, 29(4), (1997), 2131-2133.
Prochazka, et al., "Epidermal Growth Factor and Insulin Growth Factor I increase FSH-Stimulated Expansion of Porcine Cumulus Cells in Serum-free Medium", Journal of Reproduction and Fertility Abstract Series No. 25, Abstract No. 173, (Jul. 2000), 3 pgs.
Reddi, "Cartilage Morphogenesis: Role of Bone and Cartilage Morphogenetic Proteins, Homeobox Genes and Extracellular Matrix", Matrix Biology 14, (1994), 599-606.
Reddi, "Regulation of Bone Differentiation by Local and Systemic Factors", Bone and Mineral Research 3, Chapter 2, William A. Peck, editor, Elsevier Science Publishers B.V., (1985), 27-47.
Reginato, et al., "Formation of nodular structures resembling mature articular cartilage in long-term primary cultures of human fetal epiphyseal chondrocytes on a hydrogel substrate", Arthritis & Rheumatism, vol. 37, No. 9, (1994), 1338-1349.
Riesle, J, et al., "Collagen in Tissue-Engineered Cartilage: Types, Structures, and Crosslinks", J. Cell Biochem., 71(3), (Dec. 1998), 313-327.
Roberts, et al., "Transport Properties of the Human Cartilage Endplate in Relation to its Composition and Calcification", Spine vol. 21, (Feb. 15, 1996), 415-420.
Robinson, Dror, et al., "Regenerating Hyaline Cartilage in Articular Defects of Old Chickens Using Implants of Embryonal Chick Chondrocytes Embedded in a New Natural Delivery Substance", Calcified Tissue International, vol. 46, Springer-Verlag New York Inc., USA, (1990), 246-253.
Roethy, Wilfried, et al., "A Growth Factor Mixture That Significantly Enhances Angiogenesis in Vivo", The Journal of Pharmacology and Experimental Therapeutics, vol. 299, No. 2, (2001), 494-500.
Sakaguchi, et al., "A Combination of EGF and IGF-1 Accelerates the Progression of Meiosis in Bovine Oocytes In Vitro and Fetal Calf Serum Neutralizes the Acceleration Effect", Theriogenology vol. 54, (2000), 1327-1342.
Sampath, et al., "Isolation of Osteogenin, an extracellular matrix-associated, bone-inductive protein, by heparin affinity chromatography", Proc. Natl. Acad. Sci USA 84, (Oct. 1987), 7109-7113.
Sampath, T Kuber, et al., "Recombinant Human Osteo Protein-1 (hOP-1) Induces New Bone Formation in Vivo with a Specific Activity Comparable with Natural Bovine Osteogenic Protein and Stimulates Osteoblast Proliferation and Differentiation in Vitro", J. Biol. Chem. 267(28), (1992), 20352-20362.
Sasaki, Masanori, et al., "Effects of Chondroitinase ABC on Intradiscal Pressure in Sheep", Spine 26, (2001), 463-468.
Schollmeier, G, et al., "Observations on Fiber-Forming Collagens in the Anulus Fibrosus", Spine 25, (2000), 2736-2741.
Schor, S L, et al., "Motogenic activity of IGD-contianing synthetic peptides", J. Cell Science 112, (1999), 3879-3888.

(56) References Cited

OTHER PUBLICATIONS

Sellers, et al., "The Effect of Recombinant Human Bone Morphogenetic Protein-2 (rhBMP-2) on the Healing of Full-Thickness Defects of Articular Cartilage", J. of Bone and Joint Surg. 79-A(10), (1997), 1452-1463.

Skaggs, D L, et al., "Regional Variation in Tensile Properties and Biochemical Composition of the Human Lumbar Anulus Fibrosis", Spine, vol. 19, No. 12, (Jun. 15, 1994), 1310-1319.

Song, C. X, et al., "Formulation and Characterization of Biodegradable Nanoparticles for Intravascular Local Drug Delivery", Journal of Controlled Release vol. 43, No. 2/03,, XP00632668, (Jan. 18, 1997), 197-212.

Sonoda, et al., "Characterization of Tissue Healing Following Meniscal Injury and Repair: The Effect of Hyaluronan Treatment", 44th Annual Meeting, Orthopaedic Research Society, New Orleans, LA, (Mar. 1998), 887.

Spilker, Robert, et al., "A Transversely Isotropic Biphasic Finite Element Model of the Meniscus", J. Biomech., vol. 25, No. 9, (1992), 1027-1045.

Stevens, Richard, et al., "Biological Changes in the Annulus Fibrosus in Patients with Low-Back Pain", Spine 7, (1982), 223-233.

Stewart, Matthew C., et al., "Phenotypic Stability of Articular Chondrocytes In Vitro: The Effects of Culture Models, Bone Morphogenetic Protein 2, and Serum Supplemenation", Journal of Bone and Mineral Research, vol. 15, No. 1, (2000), pp. 166-174.

Stone, et al., "Regeneration of Meniscal Cartilage with Use of a Collagen Scaffold", J. of Bone and Joint Surg., 79-A(12), (1997), 1770-1777.

Stone, et al., "Surgical Technique of Meniscal Replacement", Technical Note, The Stone Clinic, (Apr. 1993), 3 pgs.

Sumida, Kenji, et al., "Serial Changes in the Rate of Proteoglycan Synthesis After Chemonucleolysis of Rabbit Intervertebral Discs", Spine 24, (1999), 1066-1070.

Suzuki, F., "Culture of Chondocytes and Ossification Mechanism", Protein, Nucleic Acid and Enzyme, vol. 23, No. 13, (1978), pp. 1302-1311.

Temple, et al., "Effect of Meniscal Repair and Hyaluronan Treatment on Cartilage Degeneration of the Femur and Tibia in the Rabbit", 45th Annual Meeting, Orthopaedic Research Society, Anaheim, CA, (Feb. 1999), 669.

Urban, J P, et al., "Chemistry of the intervertebral disc in relation to functional requirements", Grieves Modern Manual Therapy, (1994), 163-175.

Vacanti, C. A., et al., "Synthetic Polymers Seeded with Chondrocytes Provide a Template for New Cartilage Formation", Plastic and Reconstructive Surgery, vol. 88, No. 5, (1991), pp. 753-759.

Von Schroeder, Herbert P., et al., "The use of polylatic acid matrix and periosteal grafts for the reconstruction of rabbit knee articular defects", Journal of Biomedical Materials Research, vol. 25, (1991), pp. 329-339.

Wasteson, Ake, et al., "Biosythesis of Chondroitin Sulphate in Cartilage Regenerated from Perichondrium", Scan. J. Plast. Reconstr. Surg., vol. 11, (1977), pp. 17-22.

Wehling, P, et al., "Transfer of Genes to Chondrocytic Cells of the Lumbar Spine: Proposal for a Treatment Strategy of Spinal Disorders by Local Gene Thereapy", Spine 22(10), (May 15, 1997), 1092-1097.

Wittenberg, Ralf, et al., "Five-year Results From Chemonucleolysis With Chymopapain or Collagenase", Spine 26, (2001), 1835-1841.

Wolfman, et al., "Ectopic induction of tendon and ligament in rats by growth and differentiation factors 5, 6, and 7. members of the TGF-B gene family", Then American Society for Clinical Investigation Inc., vol. 100, No. 2, (1997), 321-330.

Yang, et al., "Expression of Recombinant Human BMP-6 in *Escherichia coli* and Its Purification and Bioassay in Vitro", NCBI; Shen Wu Gong Cheng Zue Bao, Chinese Journal of Biotechnology, (Sep. 2003).

Yang, Ju-Hua, et al., "Expression of recombinant human BMP-6 in *Escherichia coli* and its purification and bioassay in vitro", Chinese Journal of Biotechnology, vol. 19. (English Abstract), XP-002516116, (Sep. 2003), 2 pgs.

Yonggang, et al., "Percutaneous injection of bone morphogenetic protein and polyvinyl pyrrolidone composite", Journal of Xi 'an Medical University 22(2), (Apr. 2001), 132-133.

Yoshihashi, Yuji, et al., "Tissue Reconstitution by Isolated Articular Chondrocytes in vitro", J. Jpn. Orthop. Assoc., vol. 58, (1983), pp. 629-641.

Zhou, Shuanhu, "Demineralized bone promotes chondrocyte or osteoblast differentiation of human marrow stromal cells cultured in collagen sponges", Cell and Tissue Banking, (2005), 34-43.

Zimber, Michael P., et al., "TGF-B Promotes the Growth of Bovine Chondrocytes in Monolayer Culture and the Formation of Cartilage Tissue on Three-Dimensional Scaffolds", Tissue Engineering, vol. 1, No. 3, (1995), pp. 289-300.

Ahrendt, G., et al., "Angiogenic Growth Factors: A Review for Tissue Engineering", Tissue Engineering, 4(2), (1998), 117-130.

Fiedler, Walter, et al., "Vascular Endothelial Growth Factor, a Possible Paracrine Growth Factor in Human Acute Myeloid Leukemia", Blood, vol. 89(6), (Mar. 1997), 1870-1875.

Hammerman, Marc R, "Growth Factors in Renal Development", Seminars in Nephrology, 15, (1995), 291-299.

Herpin, Amaury, et al., "Transforming Growth Factor-Beta-Related Proteins: An Ancestral and Widespread Superfamily of Cytokines in Metazoans", Developmental & Comparative Immunology, 28(5), (2004), 461-485.

Pouliquen, et al., "Coral substituted for bone grafting in posterior vertebral arthrodesis in children", French Journal of Orthopaedic Surgery, vol. 3, No. 3, (1989), 272-280.

Ripamonti, U., et al., "Induction of bone in composites of osteogenin and porous hydroxyapatite in baboons.", Plast Reconstr Surg., 89(4), (Apr. 1992), 731-740.

Ripamonti, U., et al., "Initiation of heterotopic osteogenesis in primates after chromatographic adsorption of osteogenin, a bone morphogenetic protein, onto porous hydroxyapatite.", Biochemical and Biophysical Research Communications, 193(2), (1993), 509-517.

\* cited by examiner

RAPID ISOLATION OF OSTEOINDUCTIVE PROTEIN MIXTURES FROM MAMMALIAN BONE TISSUE

CROSS-REFERENCE TO RELATED APPLICATIONS

This application is a continuation of U.S. patent application Ser. No. 11/553,640, filed Oct. 27, 2006, now issued as U.S. Pat. No. 7,622,562, which is a continuation-in-part of U.S. patent application Ser. No. 10/606,190, now issued as U.S. Pat. No. 7,241,874, filed Jun. 25, 2003, which claims priority to U.S. Patent Application Ser. No. 60/391,566, filed Jun. 26, 2002, the disclosures of which are hereby incorporated by reference.

FIELD OF THE INVENTION

The present invention relates generally to methods for the rapid, high yield recovery and isolation of bone morphogenetic proteins (BMPs) and other tissue-inductive proteins from mammalian bone. In another aspect, the invention relates to protein mixtures recovered from bone demineralization waste streams. The invention also comprises protein mixtures produced according to the foregoing methods, and to implantable devices for osteoinductive repair of bone and tendon repair or reconstruction.

BACKGROUND OF THE INVENTION

Mammalian bone tissue comprises a number of proteins, including structural proteins such as collagen as well as osteoinductive proteins that induce or promote bone growth. Recognition of the existence of osteoinductive proteins in bone tissue has led to the discovery of a family of protein molecules known as the Bone Morphogenetic Proteins (BMPs). BMPs are members of the TGF β superfamily of proteins, which includes additional proteins that provide tissue-inductive responses in vivo, including TGF-β1, TGF-β2, and TGF-β3. Structures for proteins designated BMP-1 through BMP-18 have been isolated and additional related proteins found. Additional information regarding the BMPs can be found in U.S. Pat. Nos. 6,511,958 and 6,514,514, which are hereby incorporated by reference. The unique inductive activity of the BMPs, along with their presence in bone tissue, suggests they are involved in the regulation of bone repair processes and possibly in the normal maintenance of healthy bone tissue. There is a great need for such proteins for the induction and/or augmentation of bone growth following surgical bone repair or reconstruction procedures in human and animal patients.

Much research has been directed to producing, either by recombinant DNA techniques or by purification of naturally occurring proteins, specific osteoinductive proteins and protein mixtures. Protein mixtures having BMPs and other inductive proteins may be isolated from bone tissue according to known procedures. One of the earliest such procedures is disclosed in U.S. Pat. No. 4,294,753 to Urist, which provides a process for isolating bone proteins from bone tissue by demineralizing the bone tissue in acid. The demineralized collagen bone matrix is reduced to gelatin by adding a mineral salt. Osteoinductive BMPs are extracted from the gelatin using a solubilizing agent, such as guanidine hydrochloride and/or urea. The solubilized proteins are then purified by dialysis and several washing steps.

The processes disclosed in the '753 patent are also inherently inefficient. The demineralization step—the first step in the BMP isolation procedure—involves contacting the bone with hydrochloric acid to dissolve the mineral components of the bone and separate them from the protein components. The mineralized acid medium is discarded. Because BMPs are soluble in acids, a significant fraction of the BMPs can be lost from the beginning of processing.

The chemical reagents used to solubilize and extract the osteoinductive proteins from the demineralized bone in the '753 procedures, i.e., guanidine hydrochloride (GuHCl) and urea, are cytotoxic. Consequently, the bone proteins must be subjected to extensive and time-consuming purification procedures to ensure that the BMPs obtained by the isolation procedures are free of cytotoxic agents and remain osteoinductive when administered to the patient.

U.S. Pat. No. 4,619,989, also to Urist, discloses an improved process for isolating BMPs that involves additional dialysis purification steps beyond those disclosed in the '753 patent. Such steps increase still further the time required to isolate usable BMP mixtures. In addition, the additional purification steps further reduce protein yield and, worse still, may remove BMP fractions that are either osteoinductive per se or have a synergistic effect with the remaining BMP proteins.

An improved method of isolating and purifying BMP-containing mixtures is described in U.S. Pat. Nos. 5,290,763 and 5,371,191. Both the '763 and '191 patents disclose a multistep process to provide highly purified BMP-containing mixtures. The process involves demineralization, protein extraction, high and low molecular weight ultrafiltration steps, an anion exchange process, a cation exchange process, and a reverse-phase HPLC process. Although the resulting BMP-containing mixture is highly osteoinductive, the process is lengthy, requires expensive equipment; and has low yields.

There remains a need for BMP mixtures that may be easily, quickly and economically isolated from bone tissue in high yields, promote rapid osteoinduction when implanted in a human or animal patient; and that are amenable to combination with a wide variety of carriers.

It is an object of the present invention to provide a rapid, efficient; and economical process for obtaining osteoinductive BMP mixtures from mammalian bone tissue.

It is another object of the present invention to provide processes for recovering osteoinductive BMPs from bone demineralization waste streams.

It is another object of the invention to provide a process for obtaining osteoinductive BMP mixtures in high yields from mammalian bone tissue.

It is a still further object of the invention to provide a method of isolating osteoinductive BMP mixtures from mammalian bone tissue that minimizes loss of BMPs from the bone tissue source.

It is a further object of the invention to provide a method of isolating osteoinductive BMP mixtures from mammalian bone tissue that minimizes or avoids altogether the use of time-consuming dialysis procedures.

It is a further object of the invention to provide protein mixtures prepared by the foregoing processes.

It is a further object of the invention to provide compositions and/or implantable devices comprising a mixture of BMPs isolated from mammalian bone tissue.

SUMMARY OF THE INVENTION

In one embodiment, the present invention comprises an improved and simplified process for the rapid, high yield recovery and isolation of osteoinductive BMPs from mammalian bone. In particular, the method comprises providing clean bone particles, demineralizing the particles in a demineralization medium to provide demineralized bone matrix (DBM) particles, extracting BMPs from the DBM particles with an extracting agent removing undesired high and low molecular weight compounds, and purifying the BMPs to obtain the BMP mixtures either in a solvent or in a solid form.

It is believed that about 75% of the osteoinductive proteins in bone tissue remain bound to the bone collagen during bone demineralization, and may subsequently be recovered by conventional extraction processes known in the art. The 25% of inductive proteins that are lost due to acid solubilization during bone demineralization constitutes a significant loss of osteoinductive proteins and activity. Accordingly, in one aspect, the invention provides a method to additionally recover and isolate the BMPs from this acid waste fraction.

Demineralization yields an acidic solution of solubilized bone mineral and osteoinductive bone matrix proteins, and insoluble demineralized bone powder. Because of fundamental differences in solution and matrix chemistry, separate processing protocols are described to facilitate extraction and recovery of osteoinductive proteins from the soluble and insoluble components of the demineralization process.

In a preferred embodiment, clean bone particles or fragments are demineralized with a suitable acid, preferably hydrochloric acid, at a low pH (less than about 3.5). Hydrochloric acid is both highly acidic and can be substantially completely eliminated from a product by gaseous evolution during lyophilization. Some BMPs may be extracted from the bone tissue by the demineralizing solution. Accordingly, the acid supernatant comprising the extracted mineral components of the bone tissue also comprises BMPs and, in one embodiment of the invention, is further treated to recover osteoinductive proteins therefrom. However, a separate protein extraction agent is also preferably employed to better extract the proteins from the demineralized bone particles after separation from the mineralized supernatant. In particular, BMPs are preferably extracted from the DBM particles using guanidine hydrochloride (GuHCl), although urea or other chaotropes or mixtures thereof may also be used as a protein extraction agent.

The GuHCl extract solution is filtered or centrifuged to remove large particles, and preferably subjected to two ultrafiltration steps, preferably tangential flow filtration (TFF). In the first ultrafiltration step, high molecular weight compounds are removed in a High Molecular Weight Ultrafiltration (HMWU) step. An ultrafiltration membrane having a nominal molecular weight cut off (MWCO) of 100 kD is preferably employed, although other nominal MWCO membranes (e.g., 60, 70, 80, 90, 110, or 120 kD) may alternatively be used.

The retentate (larger particles) is discarded and the filtrate is subjected to a second ultrafiltration step to remove low molecular weight compounds in a Low Molecular Weight Ultrafiltration (LMWU) step. An ultrafiltration membrane preferably having a nominal MWCO of about 8 kD is preferred, although larger or smaller nominal MWCO membranes (e.g., 5 kD), 7 kD, 10 kD, 12 kD, or 15 kD) may be used.

The desired osteoinductive BMPs are separated from the protein extraction agent by one or more filtration steps, preferably one or more diafiltration steps. Because removal of GuHCl is especially important, the BMPs are diafiltered into low concentration GuHCl solution. To remove the remaining chaotrope, the final purification of the BMP mixtures is preferably performed by one or more purification steps such as lyophilization or precipitation. The purified BMP mixture may be redissolved in a suitable carrier liquid, such as 10 mmol HCl, or may be recovered in solid form, e.g., lyophilization, before packaging.

In another embodiment, the invention comprises a method for purifying BMP from bone tissue comprising demineralizing bone particles by contacting the bone particles with an acidic demineralization medium, extracting BMPs from the demineralized bone particles with an extracting agent, removing compounds having a molecular weight greater than a desired upper molecular weight threshold (e.g., 100 kD) by a high molecular weight filtration step, removing compounds having a molecular weight below a desired lower molecular weight threshold (e.g., 8 kD) by a low molecular weight filtration step, and recovering BMPs from the filters. Optionally, additional purification steps such as lyophilization, resuspension and/or precipitation may be performed.

In another aspect, the present invention comprises methods for recovery of osteoinductive BMPs from a bone demineralization waste stream. More particularly, the present invention comprises contacting bone particles with an acidic demineralization medium, separating the mineralized supernatant solution from the demineralized bone particles, optionally removing at least a portion of the minerals from the mineralized supernatant solution to provide a protein supernatant solution, extracting BMPs by contacting the protein supernatant solution with a protein extraction agent, removing undesired high and low molecular weight compounds, purifying the BMPs, and recovering the BMPs either in a liquid solvent or in a solid form.

In a further embodiment, the invention comprises methods for recovering osteoinductive BMPs from a bone demineralization medium. One such method comprises demineralizing bone particles in an acid medium, separating the demineralized bone particles from the mineral-containing acid supernatant, and recovering BMPs from the mineralized acid supernatant. The mineral-containing acid supernatant may be treated with a mineral precipitation agent to remove at least a portion of the mineral from the supernatant, providing a protein supernatant solution. The BMPs may be extracted from the protein supernatant with a protein extraction agent, and recovered from the extracted protein medium by removing undesired high and low molecular weight compounds, purifying the BMPs, and recovering the BMPs either in a liquid solvent or in a solid form.

In another embodiment, the invention comprises an osteogenic implant device for promoting or augmenting bone growth. The device comprises BMP mixtures obtained by the rapid purification methods described herein and an acidic matrix. In one embodiment, the acidic matrix comprises collagen and an acidic calcium phosphate salt.

DETAILED DESCRIPTION OF THE INVENTION

In one embodiment of the present invention, the process for producing BMP mixtures comprises providing clean bone tissue particles, demineralizing the particles, extracting BMPs from the particles, removing high and low molecular weight components by ultrafiltration, and purifying the BMP mixture by diafiltration, lyophilization and/or precipitation.

The starting material for the present process is mammalian bone, including human bone. Non-human animal bone; examples of which include but are not limited to bovine, ovine equine or porcine bone, may also be used, however, because it is readily available at low cost. Bovine bone is preferred. Cortical bone tissue is preferred, although cancellous bone or corticocancellous bone can also be used. Human cortical bone tissue obtained from bone banks has been cleaned and ground according to established protocols, from a documented source, and may be obtained in particle size distributions that are amenable to BMP extraction. A preferred size distribution for the particles is about 1000 μm or less.

Alternatively, starting bone tissue may be obtained, from mammalian bone obtained from, e.g., an abbatoir, by cleaning operations known in the art, such as removing all soft tissue and then grinding and further cleaning the bone. High-pressure washing is preferably employed to clean the bone tissue prior to grinding, and its use may minimize—and preferably eliminate altogether—subsequent soaking and flotation steps, as described by U.S. Pat. No. 6,627,230, to Benedict et al., incorporated herein by reference. U.S. Pat. No. 5,371,191 to Poser et al., which is hereby incorporated by reference herein in its entirety, discloses other cleaning methods for bovine bones suitable for use in the present invention. Typically, the bone is ground into successively finer particles and soaked in detergent solution to remove non-bone material. The bone is ground to particles less than 4 mm in size, preferably about 1000 μm or less. The ground bone particles are soaked in detergent solution between grindings, and rinsed in a flotation tank to remove soft tissue.

In one embodiment, soft tissue (e.g., marrow, periosteum, fat, blood, and other material) is remove from corticocancellous bone and the corticocancellous bone is pulverized to particles having a size range of about 100 μm to about 1000 μm, such as about 200 μm to about 800 μm. The particles are defatted by soaking in stirred deionized water for at least about 3 hr at about 37° C.

In a preferred embodiment, cleaned bone tissue is demineralized by soaking the particles in a suitable acid to dissolve its mineral content. Hydrochloric acid is preferred, although other acids such as formic acid, among others, can alternatively be used. A solution of dilute HCl, preferably in a range of from about 0.6 N to about 4.0N, more preferably from about 1.0 N to about 3.0 N, most preferably 2.0 N, is effective to demineralize bone. It is preferred that the pH of the demineralizing solution be controlled during demineralization at from about 0.4 to about 5.0, preferably from about 0.4 to about 2.0, more preferably at about 1.5 to prevent collagen hydrolysis.

The bone minerals and proteins are less soluble in lower acid concentrations (i.e., higher pH. Accordingly, it is theorized that low acid concentrations (or higher pH) should correspond to higher solution volumes, lower viscosity in the mixture, and higher filtration rates for the filtration steps in the process. On the other hand, the lower solubility of the proteins in lower acid concentrations also should result in higher protein loss during filtration, associated with the adhesion of proteins to the filtration membranes. Higher acid concentrations (lower pH), conversely, should result in faster mineral solubilization and smaller working solution volumes, but higher viscosity and thus slower filtration rates.

The demineralization solution may be agitated with, e.g., a stirrer, and is preferably maintained at room temperature. Additives such as $CaCl_2$ or other salts or organic solvents in which minerals are soluble, such as ethylenediamine tetraacetic acid (EDTA), can be used to enhance the solubility of the bone minerals if desired. Salts such as $CaCl_2$ are generally more effective at enhancing the solubility of the bone materials. Octyl alcohol or other defoaming agents (such as hydrocarbons such as mineral oils, white oils, or paraffins; alcohols; fatty acids; fatty acid salts of multivalent cations; esters, including fats, waxes, and phosphoric esters; amides, including amide waxes; silicone oils; and silicas) may also be used to prevent excessive foaming during demineralization. Alcohols are generally simpler to use and more effective than other materials.

The bone is soaked in acid until the bone is essentially fully demineralized. X-ray analysis may be used to evaluate the extent of demineralization. Alternatively, standard procedures can be developed through experience to determine the amount of time required for demineralization. Typically, at least two hours is required, although additional time may be required for larger batches.

In one embodiment, defatted corticocancellous bone particles are demineralized by contact with 2N HCl (pH~0.6) with stirring for at least about 3 hr at a temperature from about room temperature to about 37° C., wherein the pH of the slurry containing bone particles and HCl is kept at about pH 1.5 or less, such as from about pH 1.5 to about pH 0.6. The slurry is centrifuged, for example, at about 4000 rpm for about 12 min to about 15 min at room temperature, to yield a demineralized bone (DMB) pellet and an acid supernatant containing minerals, which may also be termed an acidic demineralization solution.

Prior an approaches, e.g., as described in U.S. Pat. Nos. 4,294,753 and 4,455,256, both of which are hereby incorporated by reference in their entirety, describe discarding the acidic demineralization solution by dialysis and washing steps. Similarly, the approach described in U.S. Pat. No. 5,371,191 also discloses discarding the HCl demineralization solution. It is believed that the high solubility of BMPs in acid results in extensive and unnecessary loss of osteoinductive proteins in prior art BMP isolation processes. Accordingly, in contrast to prior art approaches, the present invention contemplates recovery of BMPs from the mineral-containing HCl demineralization solution.

BMP recovery from the acidic demineralization solution may be accomplished by adding a protein extraction agent directly to the HCl-and-bone-tissue acidic demineralization solution, by separating the mineralized acid supernatant from the demineralized bone particles, removing at least a portion of the minerals (primarily calcium phosphate) from the mineralized supernatant solution, and adding a protein extraction agent to the supernatant to extract the BMPs and yield an extracted protein medium, or by tangential flow filtration alone. The extracted protein medium may then be purified by the same procedures as outlined herein for the extract medium for the DBM particles. Alternatively, the extracted protein medium may be combined with the extraction medium from the DBM particles at some point in the processing procedures, and all of the BMPs from the bone tissue may be recovered as a single stream.

In one embodiment, BMPs are extracted from the DMB particles (and/or solubilized in the HCl demineralization supernatant) by adding a suitable extraction agent, preferably high purity GuHCl, although urea or other extraction agents may be alternatively used. GuHCl is a preferred denaturant because it is ionic and therefore also functions well as a solubilizing agent for maintaining proteins in solution. Where GuHCl is employed, concentrations may range from 1 M to 8 M or to the solubility limits of the GuHCl. Preferred concentrations are from 2M to 8M, more preferably 4M. Lower concentrations allow less expensive extraction, as less GuHCl is used, but with slower solubilization of the BMPs and possibly lower bioactivity and/or yields.

Preferably the GuHCl extraction is performed at about body temperature (37° C.), although lower temperatures may also be used. The temperature of the denaturant can increase during the extraction process. A 4M GuHCl, pH 7.0 solution is a preferred exaction solution. Optionally, a chaotrope can be added during extraction to improve solubility of extracted proteins. Suitable chaotropes include calcium chloride ($CaCl_2$), magnesium chloride ($MgCl_2$), and cesium chloride ($CsCl_2$). Usually, extraction continues until substantially all of the noncollagenous bone proteins have been removed from the demineralized bone. A typical extraction takes about 3 hours, although higher yields can be obtained by increasing the extraction time (such as up to about 72 hr).

In one embodiment, the DMB pellet is subjected to a water wash to collect at least part of a water-soluble BMP fraction. The water wash can then be added to the demineralized acidic supernatant for further processing or it can be processed separately. The DMB pellet is then washed with PBS (phosphate buffered saline), such as 20× concentration PBS neutralized to about pH 6.5 with agitation, and the DMB and PBS wash are centrifuged, such as at 4000 rpm for about 12 min to about 15 min at room temperature. The DMB pellet is retained and the PBS wash is discarded. Multiple PBS washes can be performed, but one is frequently sufficient. The DMB pellet is then washed with deionized water to remove residual PBS salts and the DMB pellet is separated by centrifugation, as described above. Multiple deionized water washes, such as about three, can be performed. After the deionized water wash(es), the DMB pellet is solubilized with Tris/GuHCl, pH about 6.8 to about 7.0, with shaking for a relatively long duration, such as about 72 hr. The Tris/GuHCl-DMB slurry is then centrifuged and the GuHCl supernatant, which contains BMPs, is retained and subjected to TFF with a 1100 kDa MWCO and the permeate (which contains BMPs) is collected. The permeate is subjected to TFF with an 8 kDa MWCO and the retentate (which contains BMPs) is collected. GuHCl is substantially eliminated from the retentate by diafiltration, lyophilization, and about three or four cycles of ethanol precipitation. The final precipitate, containing BMPs, can then by lyophilized and solubilized in 10 mM HCl for storage.

Following demineralization, BMPs and other osteoinductive proteins in the demineralized bone extract solution are then separated by two ultrafiltration steps to remove proteins larger than a high molecular weight limit, preferably 100 kD, and smaller than a low molecular weight limit, preferably 8 kD. The filtration is preferably tangential flow filtration (TFF). TFF provides a rapid and efficient method for concentrating dissolved molecules, (i.e., proteins, peptides, nucleic acids, carbohydrates and other biomolecules), desalting or exchanging solution buffers and gross separation/fractionation. TFF is routinely used on solution volumes ranging from 200 ml to hundreds of liters and is capable of concentration them to volumes as small as 10 ml in a short period of time. TFF allows much faster and more convenient concentration, desalting, and fractionation than conventional dialysis, the process uses membrane filter cassettes that can be used more than once and the process can be easily scaled. Simple control of materials, membrane surface area and filtration path length allow for direct translation of conditions established during pilot scale to process or commercial scale.

TFF flow filtration can be used to eliminate soluble bone mineral components from the waste demineralization acid wash because of their extremely small size. To facilitate the effective and simultaneous recovery of a desired molecular weight range of proteins, a chaotrope or denaturing agent may be added to denature and deagglomerate the proteins. The use of a chaotrope or denaturing agent is optional. Guanidine hydrochloride is an example of a highly effective denaturing agent, but it functions effectively only at neutral pH (~7) values. Buffering the acidic waste stream to a neutral pH will stimulate the (re)precipitation of calcium phosphate mineral residues from the acid wash. Although a fraction of osteoinductive proteins may remain in solution, a fraction may be eliminated from solution during mineral precipitation because of the osteoinductive proteins' affinity for hydroxyapatite. An active protein residue can be recovered via this process. TFF filtration of the direct mineral waste solution can also allow soluble salt reduction.

Returning to the ultrafiltration steps, the extract solution is preferably first subjected to a high molecular weight ultrafiltration step in which proteins larger than the high molecular weight limit are removed. The high molecular weight ultrafiltration step advantageously separates soluble osteoinductive BMPs from high molecular weight collagens, and although the entire procedure is preferably conducted with sterile bone, instruments and reagents, the HMWU also eliminates any extraneous bacteria and other microorganisms to ensure a sterile product. Ultrafiltration steps having pore sizes smaller than most bacteria, e.g., 20 microns or less permit sterilization by filtration.

In a preferred embodiment, the HWMU step is performed in a Millipore Pellicon® Model tangential flow filtration (TFF) apparatus using a 100 kD nominal MWCO, polyether sulfone (PES) filter to minimize protein adhesion to the filter material. It is preferred to select a filter with relative low protein binding to the filter material itself. The ultrafiltration is preferably conducted at temperatures in the range of 2° C. to 50° C., preferably about 4° C. Other MWCO filters could be used, from about 50 kD to about 120 kD or even higher, as the HWMU step MWCO filter. A TFF apparatus is preferred because such systems are readily scalable to larger (i.e., commercial) batch sizes. The retentate (i.e., material having a MW greater than the nominal MWCO of the filtration apparatus) from the HMWU step is discarded.

The HMWU permeate is then subjected to a LMWU step in which proteins smaller than a low molecular weight limit are removed. The LWMU step is preferably performed in a TFF apparatus using an 8 kD nominal MWCO, PES filter, or other filer having low protein binding. Because of the small pore size of the filters in the LWMU step, it may be desirable to dialyze the filters or wash with HCl or another acid to assist in the passage of GuHCl through the filter.

Although an 8 kD MWCO filter is preferred larger or smaller nominal MWCO filters could be used, ranging from 5 kD to 15 kD, as the LMWU step MWCO filter. The ultrafiltration is preferably conducted at 4° C., although temperatures ranging from 2° C. to 50° C. (or even higher, so long as the proteins are not completely denatured or permanently inactivated) are permissible. The LWMU step yields a retentate with a mixture of proteins having molecular weights within a desired range.

The retentate from the LWMU step comprises a mixture of BMPs and other osteoinductive and non-osteoinductive proteins that may be implanted in a human or animal patient to promote bone growth. It is essential that the extraction agent be removed from the BMPs. GuHCl is removed by a diafiltration in a TFF apparatus into GuHCl at about 1.0 M. The proteins are then recovered by lyophilization, followed by precipitation with ethanol, resuspension in HCl and lyophilization. Additional purification by washing and/or reprecipitation of the BMPs from the wash medium may be provided.

The BMPs may advantageously be stored in sterile containers either as an osteoinductive solution or as a lyophilized solid. It is preferred to maintain the solution or solid either under vacuum or inert gas atmosphere such as e.g., nitrogen, hydrogen, helium, argon, or mixtures thereof.

Where the BMPs are maintained in an osteoinductive solution, the proteins may be used by adding the solution to a solid carrier such as collagen or bone chips, or by mixing the solution with a liquid or slurried carrier such as saline, blood, plasma, serum, PRP, or bone marrow aspirate.

Where the BMPs are maintained as a lyophilized solid, the proteins may be combined with another solid carrier, such as collagen, hydroxyapatite, or a composite device.

In one embodiment, the acidic demineralization supernatant derived from the demineralization step (and, optionally, supplemented with a water wash from the DMB pellet) is subjected to TFF with a 100 kDa MWCO and the permeate (which contains BMPs) is collected. The permeate is subjected to TFF with an 8 kDa MWCO and the retentate (which contains BMAPs) is collected. The retentate can be used to backwash the TFF membrane. The retentate is lyophilized, which will evaporate HCl from the retentate. Proteins, particularly including BMPs, are then precipitated from the lyophilized retentate by the use of ethanol. The precipitated proteins can then be lyophilized and resuspended in 10 mM HCl for storage. The steps of this embodiment can be performed without the addition of GuHCl or other denaturing agents and also without the addition of chaotropes.

Useful features of the present invention include the extraction of osteoinductive proteins from acid solution, as opposed to the discarding of the acid solution as reported in the art. This extraction involves the substantial separation of minerals via precipitation prior to protein extraction, as opposed to contemporaneous dialysis. The demineralized acid solution can be combined with DMB or DBM for joint protein extraction or protein extractions on the demineralized acid solution and the DNB or DBM prior to combination. The present invention can also involve the combining of osteoinductive proteins from water washes with osteoinductive proteins extracted from demineralized acid solution.

EXPERIMENTAL

Experiment 1

Demineralization of Bone Tissue

The following experimental protocol is one embodiment of the invention for isolating BMP mixtures. It has been used to isolate BMPs from human bone tissue that exhibit osteoinductive activity in rats. Other mammalian sources, preferably bovine or porcine, may also be used. All operations are conducted aseptically with sterile reagents and sterile equipment. A batch size of 100 g starting mineralized bone tissue has been used, but in commercial operation the batch size would preferably be much larger.

One hundred grams of clean, sterile mineralized human bone particles of 1000 microns or less was obtained from a certified bone bank source. The mineralized human bone powder was defatted with water heated to 37° C. In a sterile container with continuous agitation, approximately 500 ml of sterile water was added to the bone powder. The solution was warmed to 37° C. for one hour, after which the bone powder was separated from the water by centrifugation (3000 rpm for 15 minutes). The procedure was repeated twice to ensure complete lipid removal. Other lipid removal techniques known in the art may also be used, including the use of organic solvents such as alcohol, acetone, or the like. Removing lipids from the bone powder facilitates rapid and complete isolation of BMPs.

Following the defatting procedure, the bone powder was demineralized. In a sterile container with continuous magnetic stirring, approximately 500 ml of sterile 2 N HCl was added to the bone powder until the pH stabilized at 1.5. Higher concentrations of HCl (e.g., 3.0M to 5.0M) may be used but are more likely to fragment collagen molecules in the bone tissue, thus increasing viscosity and filtration time. The demineralization was allowed to proceed for about three hours after stabilization of the pH.

As the initial HCl was added, the mineral content of the bone was solubilized, increasing the pH. Initially, the pH rose rapidly, requiring frequent addition of HCl (each minute or even more frequently for the first several minutes) during the first thirty minutes of the procedure. After about thirty minutes, the pH stabilized at 1.5 and further addition of acid was not required. Demineralization may take from 1-24 hours, more preferably from 2-10 hours, and even more preferably from about 3 to about 3½ hours.

When the demineralization was complete, the acid was separated from the bone collagen by centrifugation at 3000 rpm for 20 minutes. Other separation methods known in the art may also be used, however. The supernatant was decanted for further processing, as described more fully in Experiment 6 below. After demineralization, the remaining tissue comprises primarily demineralized bone collagen containing osteoinductive proteins, and is known as demineralized bone (DMB). The DNB was washed with successive sterile water and/or phosphate buffered saline (PBS) rinses until the pH reached 7.0, indicating complete acid removal.

Each wash was conducted by suspending the DMB in about 250 ml of water or PBS per 100 g starting mineralized bone, stirring for about 20 minutes at room temperature, and then separating the wash and DMB, preferably by centrifugation as described previously. The wash solution (i.e., water or PBS) was decanted after each wash. Some osteoinductive proteins may be present in the wash supernatant, and the initial water washes may be saved and combined with the original acid supernatant from the demineralization step for later BMP recovery according to the protocol in Experiment 6 below. The number of water washes saved will depend on the anticipated or measured BMP concentration thereof. However, under the conditions described in this experiment, typically only the first water wash supernatant is saved.

Three water washings were performed on the DMB. The bone was also further rinsed once overnight with 20× concentration PBS (i.e., phosphate buffered saline having twenty times the standard phosphate buffer concentration) with magnetic stirring to raise the pH to 7.0. After rinsing with 20×PBS, the DMB was further subjected to three sterilized water rinses to remove the saline buffer. After rinsing was completed, the bone was frozen at −80 C. for 1-2 hours, and then lyophilized overnight (or longer). After lyophilization, the mass of the DMB was measured. Demineralized bone is typically about 40% of the starting mass of the mineralized bone.

The bone powder was acid demineralized according to known procedures. The previously described procedure provides one acceptable protocol. However, persons of skill in the art will readily appreciate that alternate protocols may also be followed with similar, acceptable results. However, saving the acid demineralization supernatant and/or the water wash supernatant for BMP recovery are not known in the art.

Experiment 2

Extraction of BMPs from Demineralized Bone

After demineralization, the DMB was extracted with filter-sterilized guanidine hydrochloride (GuHCl) to solubilize the BMPs. In particular, 500 ml of 4.0 M GuHCl, pH 7.0, was added to the DMB per 1.00 g starting mineralized bone. The extraction was continued for 72 hours with constant agitation in an incubator at 25° C. However, except for the extent they may deleteriously impact bone protein recovery and/or activity, extraction conditions are not critical and longer or shorter time periods and higher or lower temperatures can be used acceptably. A preferred range of extraction times is 24-96 hours. Lower temperatures, down to about 0° C. may be used so long as the reagents remain in the liquid state. Similarly, higher temperatures may be used, the upper limit being determined by the increased denaturation and/or activity loss of some of the osteoinductive proteins. For this reason, temperatures below 50° C. are preferred.

After the extraction was complete, the GuHCl and dissolved osteoinductive proteins were separated from the extracted DMB by centrifugation at 10,000 rpm for 10 minutes. The liquid supernatant was decanted for further processing. To ensure that all osteoinductive proteins were recovered, the extracted DMB was washed once with 100 ml of sterile water and centrifuged as before. The supernatant water and any additional osteoinductive proteins therein were added to the decanted GuHCl extract. Extracted DMB, essentially pure bone collagen that has been depleted of its osteoinductive proteins, is known as demineralized and devitalized bone matrix ("DVBM"). The DVBM was frozen and lyophilized as described for the demineralized bone. DVBM may be used as a matrix component for delivery of osteoinductive proteins.

Experiment 3

High and Low Molecular Weight Ultrafiltration

The GuHCl extract, optionally including the water from the rinse step, was then filtered in a HMWU step to remove high molecular weight, non-osteoinductive proteins such as collagen and large collagen fragments, preferably in a Millipore Pellicon XL TFF apparatus. The filters are preferably made of a material that does not bind proteins such as polyethersulfone (PES). A TFF apparatus with a 100 kD molecular weight cutoff (MWCO) filter was used to process the extract collected from Example 2, although other MWCO filters such as 60, 70, or 75 may be used. The GuMCl extract was circulated until the retentate was concentrated by a factor of from about two to about 100, i.e., the retentate volume ranges from one-half to one-hundred of the volume added to the TFF apparatus. In the present Example, the retentate was concentrated about ten-fold, i.e., the retentate was concentrated to about one-tenth of the volume added to the TFF apparatus. Thus, for a starting volume of about 500 ml GuHCl extract the retentate was concentrated to 50 ml.

The collected TFF permeate from the TUTU step, which contained the extracted proteins in GuHCl, was then passed through a low molecular weight TFF apparatus.

The desired proteins from the HMWU step permeate were separated from lower molecular weight compounds in a Low Molecular Weight Ultrafiltration (LMWU) step using a TFF apparatus with a filter having an 8 kD MWCO. Alternate embodiments are possible using different filter sizes, preferably in the range of from 2 kD-12 kD, more preferably 5-10 kD. It is preferred that the filter comprise non-protein-binding materials such as PES as already discussed. In contrast to the removal of high molecular weight compounds discussed above, in the removal of low molecular weight compounds the retentate, rather than the permeate, retains the desired proteins, which generally are in the range of 13-36 kD. Thus, low molecular weight compounds such as GuHCl pass through the 8 kD MWCO filter and the desired proteins are retained. In the present Example, the volume of the HMWU step permeate was about 1.8 liters. This volume was concentrated to about 50 ml. Thus, the low molecular weight TFF step may concentrate the GuHCl by a factor of from about two to about 1000, in the present Example about 36-fold. To collect any proteins bound to the filter membrane on the retentate side, the filter was back flushed with 100 mL GuHCl.

Experiment 4

Removal of GuHCl

Because GuHCl is cytotoxic, removal of GuHCl from the osteoinductive proteins is an important aspect of the present invention. This may be accomplished in the same TFF apparatus as the low molecular weight filtration step by performing one, and more preferably two, diafiltration steps to the low molecular weight filtration retentate. In the present Experiment, the GuHCl concentration was reduced by diafiltration in the LMWU apparatus by slowly adding five retentate volumes (about 0.5 liter) of 1.0 M GuHCl.

To ensure that no osteoinductive proteins were lost, the system was flushed with an additional two retentate volumes (100 ml) of 1.0 M GuHCl to provide a final retentate of about 150 ml of GuHCl containing the dissolved osteoinductive proteins.

Experiment 5

Further Purification by Lyophilization and Precipitation

The diafiltered proteins recovered in GuHCl were frozen and lyophilized to remove water, thereby providing a solid product. The proteins were further purified to ensure complete removal of GuHCl by precipitation in 200 proof ethanol. The ethanol was used to precipitate the proteins while keeping the GuHCl in solution. Fifteen volumes of cold, 200 proof ethanol were added to the protein solution and the mixture was maintained for thirty minutes with constant agitation at 120 rpm at −4° C. to precipitate the proteins and solubilize the GuHCl. The mixture was then centrifuged at 15,000 rpm for twenty minutes. The supernatant was decanted, and the precipitated proteins were rewashed with 200 proof ethanol until all GuHCl was removed. The clean protein precipitate was resolubilized in 10 mM HCl, and either stored solubilized at 4° C. or stored as a solid following lyophilization.

It will be appreciated that alternate means of final purification may be performed. In particular, it may be simpler and easier to conduct multiple diafiltrations to remove GuHCl and urea, or perform a more extensive second diafiltration using greater volumes (e.g., up to several hundred column volumes) of 10 mM HCl. All such embodiments are within the scope of the invention.

Experiment 6

Recovery of Proteins from Acid Demineralization Supernatant

In addition to the recovery of proteins from the DBM itself, BMPs may be recovered from the mineral-containing acid supernatant collected during the bone demineralization step. The mineralized supernatant comprises calcium and phosphate ions in solution with HCl, as well as the desired bone proteins. In the present Experiment, the recovery was performed by first removing at least a portion of the calcium ions by adding about 2.4 liters of 0.72M solution of sodium oxalate to the acid supernatant, precipitating calcium oxalate and buffering the pH of the acid supernatant to about 2.0. The precipitated calcium oxalate was removed by centrifugation (3000 rpm for 15 minutes). PBS (1× concentration) was then added to the solution in an amount sufficient to buffer the pH to 7.0. For about 500 ml of acid supernatant, about 800 ml of PBS was sufficient. The supernatant solution from which calcium has been removed is generally termed a protein supernatant solution.

Isolation of the BMPs from the buffered protein supernatant solution was then achieved by essentially the same processing steps as recited for the DBM itself i.e., high and low molecular weight ultrafiltration, and additional purification steps. Specifically, a HMWU step in a TFF apparatus was first performed to remove large collagen molecules and fragments from the bone demineralization step. The solution was filtered until the retentate volume was reduced from about 3700 ml to 50 ml. The desired proteins were suspended in the permeate. To ensure that as much protein as possible passed into the permeate, 60 retentate volumes (about 3 liters) of GuHCl was gradually added to the TFF apparatus while maintaining constant retentate volume.

The permeate from the HMWU step was then subjected to a LMWU step substantially as already described in Experiment 3 for the demineralized bone fraction, and further purified as described in Experiments 4 and 5. To avoid duplicative processing, in some instances the buffer/acid supernatant permeate could be combined with the permeate from the demineralized bone fraction and the two fractions could be processed together for the LMWU step, diafiltration into urea and dilute HCl, recovery, lyophilization, acetone precipitation and acid resuspension and lyophilization.

While various embodiments of the present invention have been described in detail, it is apparent that modifications and adaptations of those embodiments will occur to those skilled in the art. For example, the osteoinductive factors can be used in various applications such as treating periodontal diseases and in facial reconstruction, as well as in treating other bone and joint problems. However, it is to be expressly understood that such modifications and adaptations are within the spirit and scope of the present invention, as set forth in the following claims.

What is claimed is:

1. A method of producing an osteoinductive composition, comprising:
    contacting bone tissue with a demineralization medium consisting essentially of an acidic solution and optionally a bone mineral solubility enhancer, a defoaming agent or both to provide demineralized bone tissue and a mineralized supernatant;
    separating the mineralized supernatant from the demineralized bone tissue;
    recovering osteoinductive proteins from the mineralized supernatant; and
    combining the osteoinductive proteins with a carrier.

2. The method of claim 1, wherein the carrier comprises a solid.

3. The method of claim 2, wherein the solid carrier is selected from the group consisting of collagen, a bone derivative, hydroxyapatite or a composite device.

4. The method of claim 2, wherein the solid carrier comprises a bone derivative selected from the group consisting of bone chips or bone matrix.

5. The method of claim 2, wherein the solid carrier comprises bone matrix.

6. The method of claim 5, wherein the bone matrix comprises demineralized and devitalized bone matrix (DVBM).

7. The method of claim 1, wherein the carrier comprises a liquid.

8. The method of claim 7, wherein the liquid carrier is selected from the group consisting of saline, a blood-derivative or bone marrow aspirate.

9. The method of claim 7, wherein the liquid carrier comprises a blood derivative selected from the group consisting of whole blood, serum, plasma or platelet rich plasma (PRP).

10. The method of claim 2, wherein the liquid carrier comprises serum.

11. The method of claim 2, wherein the liquid carrier comprises saline.

12. The method of claim 1, wherein the carrier comprises a slurry.

13. The method of claim 1, further comprising storing the osteoinductive proteins as a solution or a solid prior to or after combining with the carrier.

14. The method of claim 13, wherein the osteoinductive proteins are stored sterile.

15. The method of claim 13, wherein the osteoinductive proteins are stored under vacuum or an inert gas atmosphere.

16. The method of claim 15, wherein the inert gas is selected from the group consisting of nitrogen, hydrogen, helium, argon or mixtures thereof.

17. The method of claim 13, wherein the osteoinductive proteins are stored as a solid.

18. The method of claim 17, wherein the osteoinductive proteins are lyophilized.

19. The method of claim 1, further comprising removing at least some mineral from the mineralized supernatant prior to or while recovering osteoinductive proteins.

20. The method of claim 19, wherein removing comprises performing tangential flow filtration of the mineralized supernatant.

21. The method of claim 19, wherein removing comprises contacting the mineralized supernatant with mineral precipitation agent.

22. The method of claim 1, wherein the solubility enhancer is a salt or solvent.

23. The method of claim 22, wherein the salt is $CaCl_2$ or ethylenediamine tetraacetic acid (EDTA).

24. The method of claim 1, wherein the defoaming agent is an alcohol, hydrocarbon, fatty acid, fatty acid salt of a multivalent cation, ester, amide or silicone oil or silica.

25. The method of claim 24, wherein the alcohol is octyl alcohol.

26. The method of claim 24 wherein the hydrocarbon is mineral oil, white oil or paraffin.

27. The method of claim 24, wherein the ester is a fat, wax or phosphoric ester.

28. The method of claim 24, wherein the amide is an amide wax.

29. The method of claim 1, wherein the defoaming agent is an alcohol.

* * * * *